United States Patent [19]

Lok et al.

[11] Patent Number: 5,160,717
[45] Date of Patent: * Nov. 3, 1992

[54] TITANIUM-ALUMINUM-SILICON-OXIDE MOLECULAR SIEVE COMPOSITIONS

[75] Inventors: Brent M. T. Lok, Shanghai, China; Bonita K. Marcus, Rye; Edith M. Flanigen, White Plains, both of N.Y.

[73] Assignee: UOP, Des Plaines, Ill.

[*] Notice: The portion of the term of this patent subsequent to Jan. 9, 2007 has been disclaimed.

[21] Appl. No.: 545,153

[22] Filed: Jun. 28, 1990

Related U.S. Application Data

[63] Continuation-in-part of Ser. No. 291,328, Dec. 28, 1988, abandoned, which is a continuation of Ser. No. 56,358, May 28, 1987, abandoned, which is a continuation of Ser. No. 604,155, Apr. 26, 1984, abandoned.

[51] Int. Cl.$^5$ ............................................. C01B 33/34
[52] U.S. Cl. .................................. 423/704; 423/718; 552/77
[58] Field of Search ................................ 423/326–333; 502/62, 77, 150, 242

[56] References Cited

U.S. PATENT DOCUMENTS

| | | | |
|---|---|---|---|
| 3,329,481 | 7/1967 | Young et al. | 23/111 |
| 3,941,871 | 3/1976 | Dwyer et al. | 423/326 |
| 4,358,397 | 11/1982 | Chuc | 585/467 |
| 4,410,501 | 10/1983 | Taramasso et al. | 423/326 |

FOREIGN PATENT DOCUMENTS 8210945  1/1983  European Pat. Off. .
2071071A 12/1979  United Kingdom .

OTHER PUBLICATIONS

"Can $Ti^{4+}$ Replace $Si^{4+}$ in Silicates?", Mineralogical Magazine, Sep., vol. 37, No. 287, pp. 366–369 (1969).
J. Muhlebach et al., "The Peroxo Complexes of Titanium", Inorg. Chem. 9, (1970), pp. 2381–2390.

Primary Examiner—R. Bruce Breneman

[57] ABSTRACT

Titanium-aluminum-silicon-oxide molecular sieves having three-dimensional microporous crystalline framework structures of tetrahedral oxide units $TiO_2$, $AlO_2$ and $SiO_2$ are disclosed having use as molecular sieves and as catalyst compositions in hydrocarbon conversion and other processes.

14 Claims, 4 Drawing Sheets

TITANIUM-ALUMINUM-SILICON-OXIDE MOLECULAR SIEVE COMPOSITIONS

CROSS REFERENCE TO RELATED APPLICATIONS

This application is a continuation-in-part of prior copending application Ser. No. 07/291,328 filed on Dec. 28, 1988, now abandoned which is incorporated by reference, which in turn is a continuation of application Ser. No. 07/056,358 filed on May 28, 1987, now abandoned, and which in turn is a continuation of Ser. No. 06/604,155 filed on Apr. 26, 1984, now abandoned.

FIELD OF THE INVENTION

The present invention relates to a new class of molecular sieve compositions containing titanium, aluminum and silicon in the form of framework tetrahedral oxide units. These compositions are prepared hydrothermally from reaction mixtures containing reactive sources of titanium, aluminum and silicon and preferably at least one organic templating agent.

DISCUSSION OF MOLECULAR SIEVES

Molecular sieves having crystalline structures and of the aluminosilicate type are well known to those familiar with molecular sieve technology. Both naturally occurring and synthetic aluminosilicates are known to exist and literally hundreds of such have been reported in the literature.

Although hundreds of aluminosilicates (binary molecular sieves) are known, the reports relating to ternary molecular sieves have been relatively few. Further, the reported ternary molecular sieves having titanium as a component have been even fewer and in those instances where titanium has been reported the amount contained in the molecular sieve has been relatively small or present as a deposition or surface modifying agent.

One early report of crystalline titano-silicate zeolites (Of course, these compositions are not zeolites as the term "zeolite" is commonly employed today.) is found in U.S. Pat. No. 3,329,481. The crystalline titano-silicates are described in U.S. Pat. No. 3,329,481 by the formula:

$(D_{2/n})_x \cdot TiO_2(SiO_2)_y$ wherein D is a monovalent metal, divalent metal, ammonium ion or hydrogen ion, "n" is the valence of D, "x" is a number from 0.5 to 3 and y is a number from about 1.0 to 3.5. The crystalline titano-silicate zeolites are characterized by X-ray powder diffraction patterns including all the d-spacings of one of the patterns selected from the group:

| Pattern A: | Pattern B: | Pattern C: |
|---|---|---|
| 7.6 − 7.9A | 4.92 ± 0.04A | 2.82 ± 0.03A |
| 3.2 ± 0.05A | 3.10 ± 0.04A | 1.84 ± 0.03A |

The difficulty in obtaining compositions containing titanium is evidenced by the disclosure of U.S. Pat. No. 4,358,397 which discloses modified aluminosilicates. The aluminosilicates are modified by treating an aluminosilicate with a compound derived from one or more elements of titanium, zirconium or hafnium. The resulting compositions are said to contain a minor proportion of an oxide of such elements. It is clear that in the disclosed compositions the oxides of titanium, zirconium and hafnium were present as deposited oxides and were present in a minor proportion.

Although there has been an extensive treatment in various patents and in the published literature of aluminosilicates and recently, aluminophosphates, there has been little information available on molecular sieves other than such materials. This is particularly true in the area of titanium containing compositions.

Molecular sieve compositions wherein titanium is present in the framework of the molecular sieve or is so intimately related as to change the physical and/or chemical characteristics of the molecular sieve have not been extensively reported. This is understandable in the area of aluminosilicates, as indicated by the article, "Can $Ti^{4+}$ replace $Si^{4+}$ in silicates?", Mineralogical Magazine, September vol. 37, No. 287, pages 366-369 (1969). In this article it is concluded that substitution of framework silicon by titanium does not usually occur in aluminosilicates owing to the preference of titanium to be octahedrally bound rather than tetrahedrally bound. Even in the formation of crystalline "titanosilicate zeolites", as disclosed in U.S. Pat. No. 3,329,481 and discussed above, wherein a metallosilicate complex is formed and treated to give the titanosilicate product the evidence for the claimed titanosilicate is based on the X-ray powder diffraction pattern data. However, these data are somewhat suspect as to whether they actually show substitution of titanium into the silicate framework inasmuch as the same claimed X-ray patterns are also observed for the zirconium silicates. Further, similar X-ray patterns showing similar interplanar distance for the two values in pattern B have been reported for silicalite. (see GB 2,071,071 A).

The incorporation of titanium in a silicalite-type structure is disclosed in GB 2,071,071 A, published December 21, 1979. The amount of titanium claimed to be substituted into the silicalite-type structure is very small, being no more than 0.04 mole percent, based on the number of moles of silica, and may be as low as 0.0005. The titanium content was determined by chemical analysis and was not determined to be greater than 0.023 in any of the reported examples. As indicated by a comparison of FIG. 1a and FIG. 1b of GB 2,071,071 A, the amount of titanium present is so small that no significant change in the X-ray diffraction pattern of silicalite was observed and the minor changes observed may simply be due to occluded titanium dioxide. Thus, in the absence of other analytical data the results are not well defined. No comparison data for titanium dioxide are disclosed.

In view of the above, it is clear that the substitution of titanium for silicon into a zeolitic-type framework although conceived to be possible has been viewed by those skilled in the art as most difficult to achieve. The difficulty which is met in preparing titanium-containing molecular sieve compositions is further demonstrated by the failure of European Patent Application No. 82109451.3 (Publication No. 77,522, published April 27, 1983) entitled "Titanium-containing Zeolites and Method for Their Production as well as Use of Said Zeolites", to actually prepare titanium-containing molecular sieve compositions. Although the applicants claim the preparation of titano-aluminosilicates having the pentasil structure, it is evident from an analysis of the products of the examples that titanium was not present in the form of a framework tetrahedral oxide.

The product of the example of European patent application No. 82109451.3 will be discussed in detail in a comparative example hereinafter.

Another reference which deals with titano-aluminosilicates is U.S. Pat. No. 4,410,501 to Taramasso. This reference primarily deals with the preparation of titanium silicates and only in passing does it mention a titanium/aluminum/silicon composition. The patentee presents one example (Example 8) in which it is stated that the addition of aluminum changed the characteristics of the titanium silicate. As will be shown in detail hereinafter, this change in property is owing to the fact that what Taramasso made was ZSM-5 and not a titano-aluminosilicate. In fact In contrast to this prior art applicants are the first to prepare a molecular sieve having a three-dimensional framework structure of $TiO_2$, $AlO_2$ and $SiO_2$ tetrahedral units. In particular there is nothing in the prior art to indicate that a titano-aluminosilicate can be prepared in which the titanium content is greater than 0.04 mole fraction. Further, applicants use titanium compounds which do not precipitate under the basic conditions used to prepare the molecular sieves. See e.g. J. Muhlebach et al., "The Peroxo Complexes of Titanium", Inorg. Chem. 9 (1970) pp. 2381-2390 which discloses that peroxotitanate compounds precipitate at high pH.

SUMMARY OF THE INVENTION

Figure 1:
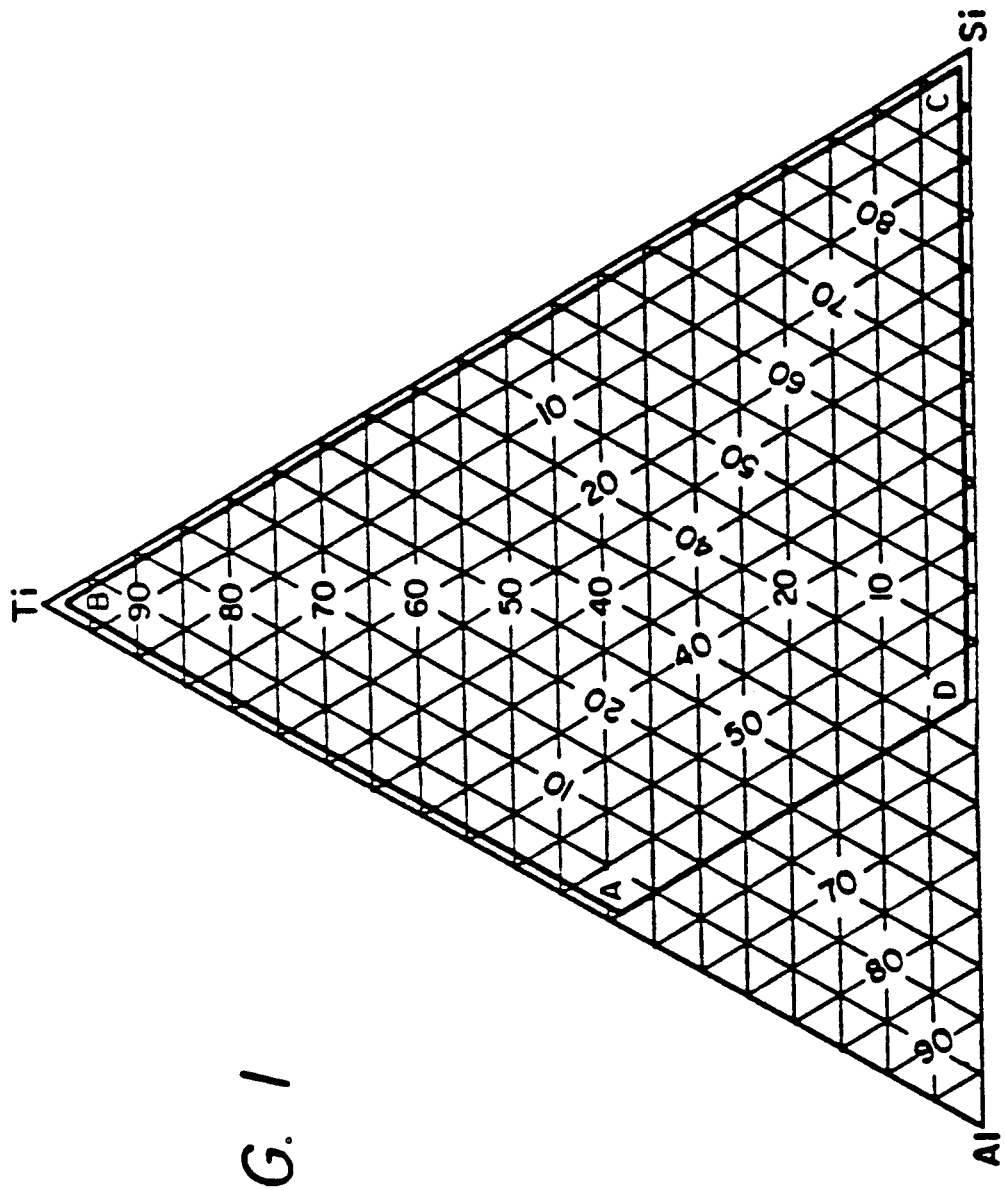
FIG. 1 is a ternary diagram wherein parameters relating to the instant compositions are set forth as mole fractions.

This invention relates to molecular sieve composition, a process for preparing the molecular sieves and a process for using the molecular sieve. Accordingly, one embodiment of the invention is a crystalline molecular sieve having a three dimensional microporous framework structure of the $TiO_2$, $AlO_2$ and $SiO_2$ tetrahedral units, having an intracrystalline pore system where the pores have nominal diameters of about 6 Angstroms and having a chemical composition on an anhydrous basis expressed by the formula:

where "R" represents at least one organic templating agent present in the intracrystalline pore system; "m" represents the moles of "R" present per mole of $(Ti_xAl_ySi_z)O_2$ and has a value from zero to about 0.3; and "x", "y", and "z" represent the mole fractions of titanium, aluminum, and silicon, respectively, present as tetrahedral oxides, said mole fractions being such that they are within the compositional area defined by points A, B, C, and D of the ternary diagram of FIG. 1 and having a characteristic X-ray pattern as set forth in Table III.

TABLE III

| 2Θ | d (Å) | Relative Intensity |
|---|---|---|
| 7.9–8.0 | 11.17–11.10 | m–vs |
| 8.8–8.9 | 10.03–9.97 | m |
| 23.1–23.3 | 3.85–3.82 | m–vs |
| 23.7–23.8 | 3.76–3.75 | m |
| 23.9–24.0 | 3.73–3.71 | m |
| 24.4–24.5 | 3.66–3.63 | m |

Another embodiment of the invention is a process for preparing the molecular sieve described above, the process comprising providing a reaction mixture composition at an effective temperature and for an effective time sufficient to produce the molecular sieve, the reaction mixture composition comprising reactive sources of aluminum, silicon and titanium, the titanium source selected from the group consisting of titanium alkoxides, water soluble titanates and titanium chelates, the reaction mixture composition expressed in terms of molar oxide ratios by the formula:

where "R" is an organic templating agent; "a" is an effective amount of "R"; "b" has a value from zero to about 5000; and "u", "v" and "w" represent the mole fractions of titanium, aluminum and silicon, respectively, in the $(Ti_uAl_vSi_w)O_2:bH_2O$ constituent, and each has a value of at least 0.01.

Yet another embodiment is a process for converting a hydrocarbon feed to a hydrocarbon converted product, which comprises contacting said hydrocarbon feed under hydrocarbon converting conditions with a molecular sieve as described above.

Other objects and embodiments of this invention will become apparent in the following detailed description.

The instant titanium-aluminum-silicon-oxides will be generally referred to herein by the acronym "TASO-45" to designate the instant titanium-aluminum-silicon-oxide molecular sieves having a framework structure of $TiO_2$, $AlO_2$ and $SiO_2$ tetrahedral oxide units. This designation is an arbitrary one and is not intended to denote structural relations to another material(s) which may also be characterized by a numbering system.

DETAILED DESCRIPTION OF THE INVENTION

The instant invention relates to a titanium-aluminum-silicon-oxide molecular sieve, a process for preparing the molecular sieve and a process for using the molecular sieve. The molecular sieves of this invention are crystalline molecular sieves having a three-dimensional microporous crystal framework structure of $TiO_2$, $AlO_2$, and $SiO_2$ tetrahedral units. By microporous is meant that the composition has an intracrystalline pore system, which pores have nominal diameters of about 6 Angstroms. The molecular sieves of this invention have a unit empirical formula on an anhydrous basis of:

wherein "R" represents at least one organic templating agent present in the intracrystalline pore system: "m" represents the moles of "R" present per mole of $(Ti_xAl_ySi_z)O_2$ and has a value from between zero to about 0.3.; and "x", "y" and "z" represent the mole fractions of titanium, aluminum and silicon, respectively, present as tetrahedral oxides, said mole fractions being such that they are within the tetragonal compositional area defined by points A, B, C and D of FIG. 1 and representing the following values for "x", "y" and "z":

| Point | Mole Fraction | | |
|---|---|---|---|
| | x | y | z |
| A | 0.39 | 0.60 | 0.01 |
| B | 0.98 | 0.01 | 0.01 |
| C | 0.01 | 0.01 | 0.98 |
| D | 0.01 | 0.60 | 0.39 |

Figure 2:
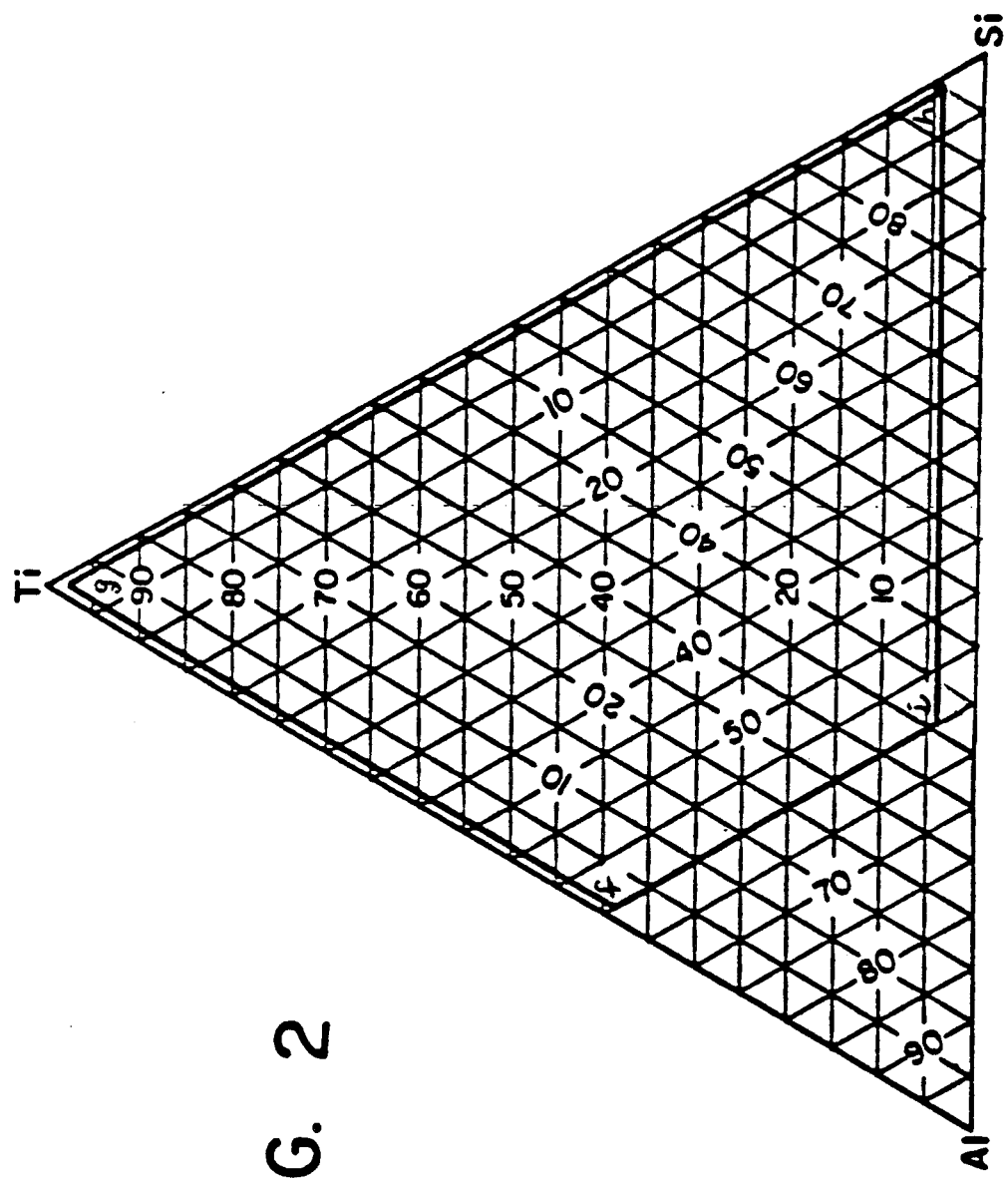
FIG. 2 is a ternary diagram wherein parameters relating to preferred compositions are set forth as mole fractions.

Preferably the parameters "x", "y" and "z" are within the tetragonal area defined by points f, g, h and i of FIG. 2 and represent the following values of "x", "y" and "z":

| Point | Mole Fraction | | |
|---|---|---|---|
| | x | y | z |
| f | 0.39 | 0.60 | 0.01 |
| g | 0.98 | 0.01 | 0.01 |
| h | 0.041 | 0.01 | 0.949 |
| i | 0.041 | 0.60 | 0.359 |

Figure 3:
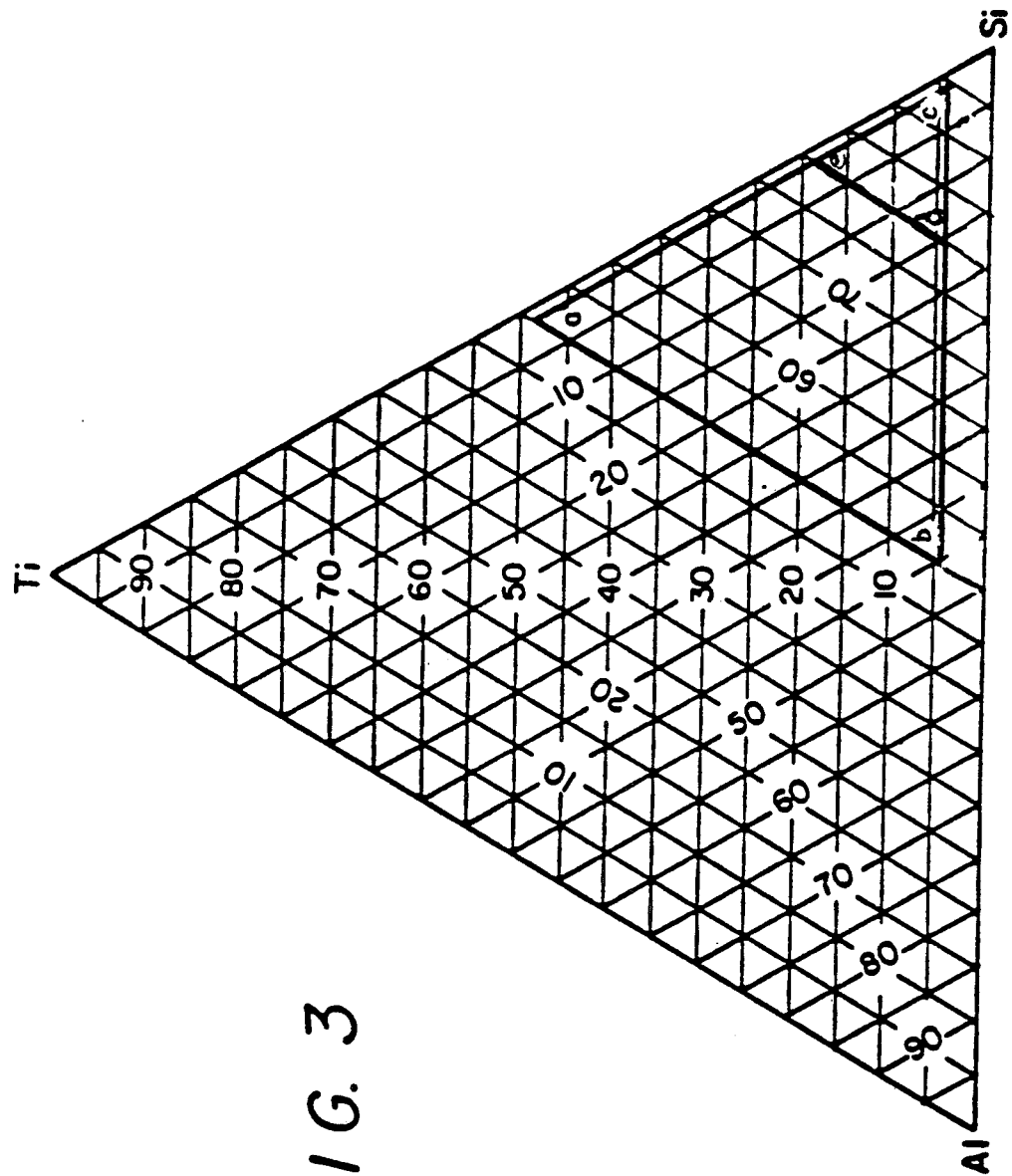
FIG. 3 is a ternary diagram wherein parameters relating to especially preferred compositions are set forth as mole fractions.

The parameters "x", "y" and "z" are more preferably within the trigonal compositional area defined by points a, b, and c of FIG. 3 of the drawings, said points a, b, and c representing the following values for "x", "y" and "z":

| Point | Mole Fraction | | |
|---|---|---|---|
| | x | y | z |
| a | 0.51 | 0.01 | 0.48 |
| b | 0.041 | 0.48 | 0.479 |
| c | 0.041 | 0.01 | 0.949 |

Finally, the parameters "x", "y" and "z" are most preferably within the trigonal compositional area defined by points c, d and e of FIG. 3 of the drawings, said points c, d and e representing the following values of "x", "y" and "z":

| Point | Mole Fraction | | |
|---|---|---|---|
| | x | y | z |
| c | 0.041 | 0.01 | 0.949 |
| d | 0.041 | 0.16 | 0.799 |
| e | 0.19 | 0.01 | 0.80 |

The term "unit empirical formula" is used herein according to its common meaning to designate the simplest formula which gives the relative number of moles of titanium, aluminum and silicon which form the $TiO_2$, $AlO_2$ and $SiO_2$ tetrahedral units within a titanium-aluminum-silicon-oxide molecular sieve and which form the molecular framework of the TASO-45 composition(s). The unit empirical formula is given in terms of titanium, aluminum and silicon as shown in Formula (1), above, and does not include other compounds, cations or anions which may be present as a result of the preparation or the existence of other impurities or materials in the bulk composition not containing the aforementioned tetrahedral units. The amount of template R is reported as part of the composition when the as-synthesized unit empirical formula is given, and water may also be reported unless such is defined as the anhydrous form. For convenience, coefficient "m" for template "R" is reported as a value that is normalized by dividing the number of moles of organic by the total moles of titanium, aluminum and silicon.

The unit empirical formula for a given TASO-45 can be calculated using the chemical analysis data for that TASO-45. Thus, for example, in the preparation of TASO-45 disclosed hereinafter the overall composition of the as-synthesized TASO-45 is calculated using the chemical analysis data and expressed in terms of molar oxide ratios on an anhydrous basis.

The unit empirical formula for a TASO-45 may be given on an "as-synthesized" basis or may be given after an "as-synthesizes" TASO-45 composition has been subjected to some post treatment process, e.g., calcination. The term "as-synthesized" herein shall be used to refer to the TASO-45 compositions(s) formed as a result of the hydrothermal crystallization but before the TASO-45 composition has been subjected to post treatment to remove any volatile components present therein. The actual value of "m" for a post-treated TASO-45 will depend on several factors (including: the particular TASO-45, template, severity of the post-treatment in terms of its ability to remove the template from the TASO-45, the proposed application of the TASO-45 composition, etc.) and the value for "m" can be within the range of values as defined for the as-synthesized TASO-45 compositions although such is generally less than the as-synthesized TASO-45 unless such post-treatment process adds template to the TASO-45 so treated. A TASO-45 composition which is in the calcined or other post-treatment form generally has an empirical formula represented by Formula (1), except that the value of "m" is generally less than about 0.02. Under sufficiently severe post-treatment conditions, e.g., roasting in air at high temperature for long periods (over 1 hr.), the value of "m" may be zero (0) or, in any event, the template, R, is undetectable by normal analytical procedures.

The molecular sieves of the instant invention are generally synthesized by hydrothermal crystallization from a reaction mixture comprising reactive sources of titanium, aluminum and silicon, and preferably one or more organic templating agents. Optionally, alkali metal(s) may be present in the reaction mixture. The reaction mixture is placed in a pressure vessel, preferably lined with an inert plastic material, such as polytetrafluoroethylene, and heated, preferably under autogenous pressure, at a temperature of from about 50° C. to about 250° C., until crystals of the molecular sieve product are obtained, usually for a period of from 2 hours to 2 weeks or more. While not essential to the synthesis of the instant molecular sieves, it has been found that in general stirring or other moderate agitation of the reaction mixture and/or seeding the reaction mixture with seed crystals of either the TASO-45 to be produced, or a topologically similar composition, facilitates the crystallization procedure. The product is recovered by any convenient method such as centrifugation or filtration.

After crystallization the TASO-45 may be isolated and washed with water and dried in air. As a result of the hydrothermal crystallization, the as-synthesized TASO-45 contains within its intracrystalline pore system at least one form of any template employed in its formation. Generally, the template is a molecular species, but it is possible, stearic considerations permitting, that at least some of the template is present as a charge-balancing cation. Generally the template is too large to move freely through the intracrystalline pore system of the formed TASO-45 and may be removed by a post-treatment process, such as by calcining the TASO-45 at temperatures of between about 200° C. and to about 700° C. so as to thermally degrade the template or by employing some other post-treatment process for removal of at least part of the template from the TASO-45. In some instances the pores of the TASO-45 are sufficiently large to permit transport of the template, and, accordingly, complete or partial removal thereof can be accomplished by conventional desorption procedures such as carried out in the case of zeolites.

Figure 4:
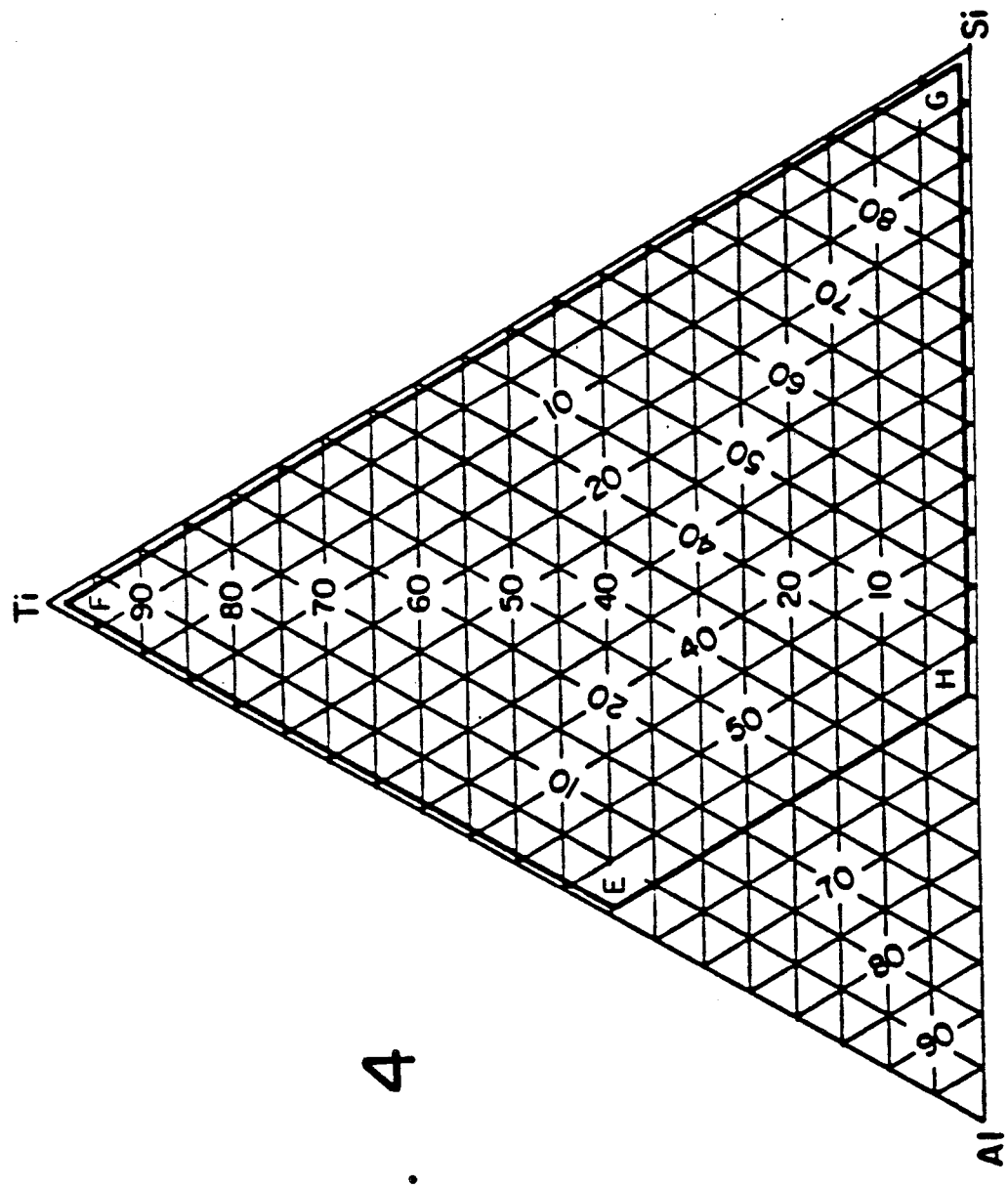
FIG. 4 is a ternary diagram wherein parameters relating to the reaction mixtures employed in the preparation of the compositions of this invention are set forth as mole fractions.

TASO-45 compositions are formed from a reaction mixture containing reactive sources of $TiO_2$, $Al_2O_3$, and $SiO_2$ and an organic templating agent, said reaction mixture comprising a composition expressed in terms of molar oxide ratios of:

$aR_2O:(Ti_uAl_vSi_w)O_2:b\ H_2O$ where "R" is an organic templating agent; "a" has a value large enough to constitute an effective amount of "R" said effective amount being that amount which form said TASO-45 compositions and preferably has a value of from greater than zero to about 100 and more preferably between about 1 and about 50; "b" has a value from greater than zero to 5000, preferably from about 50 to about 400: "u", "v" and "w" represent the mole fractions, respectively, of titanium, aluminum and silicon in the $(Ti_uAl_vSi_w)O_2$ constituent, and each has a value of at least 0.01 and being within the tetragonal compositional area defined by points E, F, G, and H of FIG. 4 of the drawings, said points E, F, G, and H representing the following values for "u", "v" and "w":

| Point | Mole Fraction | | |
|-------|------|------|------|
|       | u    | v    | w    |
| E     | 0.39 | 0.60 | 0.01 |
| F     | 0.98 | 0.01 | 0.01 |
| G     | 0.01 | 0.01 | 0.98 |
| H     | 0.01 | 0.60 | 0.39 |

Preferably "u" varies from greater than 0.04 to 0.98, "v" varies from 0.01 to 0.60 and "w" varies from 0.01 to 0.95 and when v=0.60, w=0.36.

The reaction mixtures from which TASO-45 is formed generally contain one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen and are of the formula $R_4S^+$ wherein X is selected from the group consisting of nitrogen, phosphorus, arsenic and/or antimony and R may be hydrogen, alkyl, aryl, aralkyl or alkylaryl group and is preferably aryl or alkyl containing between 1 and 8 carbon atoms.

Nitrogen-containing templates are preferred, including amines and quaternary ammonium compounds, the latter being represented generally by the formula $R'_4N^+$ wherein each R' is an alkyl, aryl, alkylaryl, or aralkyl group; wherein R' preferably contains from 1 to 8 carbon atoms when R' is an alkyl group. Polymeric quaternary ammonium salts such as $[(C_{14}H_{32}N_2)(OH)_2]_x$ wherein "x" has a value of at least 2 may also be employed. The mono-, di- and tri-amines, including mixed amines, may also be employed as templates either alone or in combination with a quaternary ammonium compound, quaternary phosphonium compound or another template. The exact relationship of various templates when concurrently employed is not clearly understood.

Representative templates which may be employed include: tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; 1,4-diazabicyclo (2,2,2) octane; N-methyldiethanolamine; N-methyl-ethanolamine; N-methylcyclohexylamine; 3-methyl-pyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone.

If an alkoxide is selected as the reactive aluminum, silicon or titanium source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of TASO-45, although such may be acting as templates.

Alkali metal cations if present in the reaction mixture may facilitate the crystallization of TASO-45, although the exact function of such cations, when present, in crystallization, if any, is not presently known. Alkali cations present in the reaction mixture generally appear in the formed TASO-45 composition, either as occluded (extraneous) cations and/or as structural cations balancing net negative charges at various sites in the crystal lattice. It should be understood that although the unit formula for TASO-45 does not specifically recite the presence of alkali cations they are not excluded in the same sense that hydrogen cations and/or hydroxyl groups are not specifically provided for in the traditional formulae for zeolitic aluminosilicates.

The reactive source of titanium which may be used is a titanium compound which does not precipitate under the basic conditions employed to crystallize the molecular sieves of this invention. These compounds are selected from the group consisting of titanium alkoxides, water-soluble titanates and titanium chelates. Illustrative of these compounds are titanium isopropoxide, titanium bis(2,4-[pentanedionate-O-O') bis (2-propanolato), ethanol, 2,2'2''-nitrilotris-titanium(IV), titanate(2-dihydroxy bis[2-hydroxypropanato(2)-O$^1$O$^2$], titanium bis(ethyl- 3-oxobutanolato-O$^1$,O$^3$)bis(2-propanolato), titanium bis(2,4-pentanedionato-O,O$^1$)-bis(2-propanolate), etc.

Most any reactive source of silicon can be employed herein. The preferred reactive sources of silicon are silica, either as a silica sol or as fumed silica, a reactive solid amorphous precipitated silica, silica gel, alkoxides of silicon, silicic acid or alkali metal silicate and mixtures thereof.

Most any reactive aluminum source may be employed herein. The preferred reactive aluminum sources include aluminum alkoxides, such as aluminum isopropoxide, and pseudoboehmite. Crystalline or amorphous aluminosilicates which are a suitable source of silicon are, of course, also suitable sources of aluminum. Other sources of aluminum used in zeolite synthesis, such as gibbsite, sodium aluminate and aluminum trichloride, may also be used.

The following examples are provided to exemplify the invention and are not meant to be limiting thereof in any way.

EXAMPLES 1-66

(a) Examples 1 to 66 were carried out to demonstrate the preparation of the TASO-45 compositions of this invention. The TASO-45 compositions were prepared by employing the hydrothermal crystallization procedure discussed supra. Reaction mixtures were prepared for each example using one or more of the following preparative reagents:

(1) Tipro: Titanium isopropoxide;
(2) AA: TYZOR AA, Titanium, bis(2,4-pentanedionate-O,O') bis(2-propanolato)-;
(3) TE: TYZOR TE, Ethanol, 2,2', 2''-nitrilotris-, titanium (4+) salt;
(4) LA: TYZOR LA, Titanate (2-), dihydroxy bis [2-hydroxypropanato(2)-$O^1O^2$]-;
(5) DC: TYZOR DC, Titanium bis(ethyl-3-oxobutanolate-$O^1,O^3$)bis (2-propanolate)-;
(6) ANF: TYZOR ANF, Titanium, bis(2,4-pentanedionato-O,O')bis(2-propanolate)-;
(7) LUDOX-LS: Trademark Of Dupont for an aqueous solution of 30 weight percent $SiO_2$ and 0.1 weight percent $Na_2O$;
(8) Sodium aluminate;
(9) Sodium hydroxide;
(10) TBABr: tetrabutylammonium bromide;
(11) TEABr: tetraethylammonium bromide;
(12) TPABr: tetrapropylammonium bromide:
(13) TPAOH: tetrapropylammonium hydroxide;
(14) Kaiser alumina.

The designation TYZOR in the above list is the trademark of DuPont for the identified titanium compounds. The method of addition of the above mentioned components to the reaction mixture was done according to three methods (A, B and C). In some of the examples seed crystals of silicalite (U.S. Pat. No. 3,941,871) were added to the reaction mixtures. Methods A, B and C are as follows:

METHOD A

LUDOX-LS and two-thirds of the water were blended to form a homogeneous mixture. The remaining water and sodium hydroxide were blended to form a homogeneous mixture. Sodium aluminate was dissolved in this second mixture and the two mixtures blended to form a homogeneous mixture. The titanium source was blended into this mixture after which the organic templating agent (referred to herein as "template") was added to this mixture and blended until a homogeneous mixture was observed.

METHOD B

LUDOX-LS and one half of the water were blended to form a homogeneous mixture. The titanium source was added to this mixture and blended to form a homogeneous mixture. The sodium aluminate was dissolved in approximately one fourth the water and added to the previous mixture until a homogeneous mixture was observed. The sodium hydroxide was dissolved in one fourth of the water and blended with the previous mixture. The organic template was added to this mixture and blended until a homogeneous mixture was observed.

METHOD C (a) LUDOX-LS and one-third of the water were blended to form a homogeneous mixture. The sodium hydroxide was dissolved in one-sixth of the water and added to this mixture and blended to form a homogeneous mixture. Kaiser alumina was dissolved in one-sixth of the water added to the NaOH solution and blended. The mixture was then added to the LUDOX solution and blended. The titanium source was added to this mixture and blended to provide a homogeneous mixture after which the organic template (in one-third of the water) was added and the mixture again blended until a homogeneous mixture was observed.

(b) The X-ray patterns appearing herein were obtained using standard X-ray powder diffraction techniques or by use of copper K-alpha radiation with computer based techniques using Siemens D-500 X-ray powder diffractometers, Siemens Type K-805 X-ray sources, available from Siemens Corporation, Cherry Hill, N.J., with appropriate computer interface. The standard X-ray technique employs as the radiation source a high-intensity, copper target, X-ray tube operated at 50 Kv and 40 ma. The diffraction pattern from the copper K radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as $2\Theta$ (theta) where theta is the Bragg angle as observed on the strip chart. Intensities were determined from the heights of diffraction peaks after subtracting background. "$I_o$" being the intensity of the strongest line or peak, and "I" being the intensity of each of the other peaks. When Relative Intensities are reported the following abbreviations mean: vs=very strong; s=strong; m=medium, w=weak; and vw=very weak. Other abbreviations include: sh=shoulder and br=broad. In terms of $100 \times I/I_o$ the above designations are defined as vs=80-100; s=60-80; m=15-60; w=0-15.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art.

(c) The preparative examples were carried out by preparing reaction mixtures having molar amounts of components expressed by:

e R:f $Al_2O_3$:g $SiO_2$:h $TiO_2$:i NaOH:j $H_2O$ wherein "R" is at least one organic template as hereinbefore defined; and e, f, g, h, i and j are the number of moles of template, $Al_2O_3$, $SiO_2$, $TiO_2$, NaOH and $H_2O$, respectively. The values for e, f, g, h, i and j are set forth in Table 1 for the TASO-45 products prepared in Examples 1 to 66.

TABLE I[1]

| Example | Template | g | h | i | j | Temp (°C.) | Time (days) | Ti Source | Mix Method[2] |
|---|---|---|---|---|---|---|---|---|---|
| 1 | TPABr | 15 | 10 | 14 | 1715 | 150 | 14 | TiPro | B |
| 2 | TPABr | 15 | 10 | 14 | 1715 | 200 | 4 | TiPro | B |
| 3 | TPABr | 15 | 10 | 14 | 1715 | 200 | 14 | TiPro | B |
| 4 | TPAOH | 35 | 5 | 10 | 1779 | 150 | 4 | AA | B |
| 5 | TPAOH | 35 | 5 | 10 | 1779 | 150 | 14 | AA | B |
| 6 | TPAOH | 35 | 5 | 10 | 1779 | 150 | 20 | AA | B |
| 7 | TPAOH | 35 | 5 | 10 | 1779 | 200 | 4 | AA | B |
| 8 | TPAOH | 35 | 5 | 10 | 1779 | 200 | 10 | AA | B |
| 9 | TPAOH | 35 | 5 | 10 | 1779 | 150 | 4 | AA | A |
| 10 | TPAOH | 35 | 5 | 10 | 1779 | 150 | 10 | AA | A |
| 11 | TPAOH | 35 | 5 | 10 | 1779 | 200 | 4 | AA | A |
| 12 | TPAOH | 35 | 5 | 10 | 1779 | 200 | 10 | AA | A |
| 13 | TPAOH | 35 | 5 | 10 | 1715 | 150 | 4 | TE | A |
| 14 | TPAOH | 35 | 5 | 10 | 1715 | 150 | 10 | TE | A |
| 15 | TPAOH | 35 | 5 | 10 | 1715 | 150 | 4 | TE | B |
| 16 | TPAOH | 35 | 5 | 10 | 1715 | 150 | 10 | TE | B |
| 17 | TPAOH | 35 | 5 | 10 | 1750 | 150 | 4 | LA | A |
| 18 | TPAOH | 35 | 5 | 10 | 1750 | 150 | 10 | LA | A |
| 19 | TPAOH | 35 | 5 | 10 | 1784 | 150 | 4 | LA | B |
| 20 | TPAOH | 35 | 5 | 10 | 1784 | 150 | 10 | LA | B |

[1] All amounts are given in moles. The value of "e" was 3.6 and the value of "f" was 1.0.
[2] Seed crystals of silicalite were added after formation of the reaction mixture in examples 1 to 20. The seed crystals were present in an amount of five wt. percent based on the weight of the solid oxides of the reaction mixture, exclusive of the seed crystals.

| Example | Template | e | i | j | Temp (°C.) | Time (days) | Ti Source | Mix Method[2] |
|---|---|---|---|---|---|---|---|---|
| 21 | TPAOH | 3.6 | 14 | 1715 | 150 | 4 | Tipro | B |
| 22 | TPAOH | 3.6 | 14 | 1715 | 150 | 11 | Tipro | B |
| 23 | TPAOH | 3.6 | 14 | 1715 | 200 | 4 | Tipro | B |
| 24 | TPAOH | 3.6 | 14 | 1715 | 200 | 11 | Tipro | B |
| 25 | TPAOH | 3.6 | 14 | 1715 | 150 | 4 | DC | A |
| 26 | TPAOH | 3.6 | 14 | 1715 | 150 | 11 | DC | A |
| 27 | TPAOH | 3.6 | 14 | 1715 | 200 | 4 | DC | A |
| 28 | TPAOH | 3.6 | 14 | 1715 | 200 | 11 | DC | A |
| 29 | TPAOH | 25.2 | 3.6 | 1800 | 200 | 21 | Tipro | A |
| 30 | TPAOH | 3.6 | 7 | 1715 | 150 | 18 | Tipro | A |
| 31 | TPAOH | 3.6 | 7 | 1715 | 200 | 10 | Tipro | A |
| 32 | TPAOH | 3.6 | 7 | 1715 | 200 | 18 | Tipro | A |
| 33 | TPAOH | 3.6 | 14 | 1715 | 150 | 5 | Tipro | A |
| 34 | TPAOH | 3.6 | 14 | 1715 | 150 | 10 | Tipro | A |
| 35 | TPAOH | 3.6 | 14 | 1715 | 200 | 5 | Tipro | A |
| 36 | TPAOH | 3.6 | 14 | 1715 | 200 | 10 | Tipro | A |
| 37 | TPAOH | 3.6 | 14 | 1715 | 200 | 4 | Tipro | A |
| 38 | TPAOH | 3.6 | 14 | 1715 | 200 | 4 | Tipro | A |
| 39 | TPAOH | 3.6 | 14 | 1715 | 150 | 4 | Tipro | A |

[1] All amounts are given in moles. The value of "f" was 1.0, "g" was 35 and "h" was 5.
[2] Seed crystals of silicalite were added after formation of the reaction mixture in examples 21 to 28 and 37 to 39. The seed crystals were present in an amount of five wt. percent based on the weight of the solid oxides of the reaction mixture, exclusive of the seed crystals.

| Example | Template | f | g | h | i | j | Temp (°C.) | Time (days) | Ti Source | Mix Method[2] |
|---|---|---|---|---|---|---|---|---|---|---|
| 40 | TPAOH | 1.0 | 35 | 5 | 14 | 1715 | 150 | 3 | Tipro | A |
| 41 | TPAOH | 1.0 | 35 | 5 | 14 | 1715 | 150 | 7 | Tipro | A |
| 42 | TPAOH | 1.0 | 35 | 5 | 14 | 1715 | 150 | 10 | Tipro | A |
| 43 | TPAOH | 1.0 | 35 | 5 | 14 | 1715 | 125 | 4 | Tipro | B |
| 44[3] | TPABr | 0.71 | 80 | 2 | 10.5 | 1912 | 150 | 4 | TE | C |
| 45[3] | TPABr | 0.71 | 80 | 2 | 10.5 | 1912 | 150 | 10 | TE | C |
| 46[3] | TPABr | 0.71 | 80 | 2 | 10.5 | 1912 | 200 | 4 | TE | C |
| 47[3] | TPABr | 0.71 | 80 | 2 | 10.5 | 1912 | 200 | 10 | TE | C |
| 48[3] | TPABr | 0.71 | 80 | 2 | 10.5 | 1717 | 150 | 4 | Tipro | C |
| 49[3] | TPABr | 0.71 | 80 | 2 | 10.5 | 1717 | 150 | 10 | Tipro | C |
| 50[3] | TPABr | 0.71 | 80 | 2 | 10.5 | 1717 | 200 | 4 | Tipro | C |
| 51[3] | TPABr | 0.71 | 80 | 2 | 10.5 | 1717 | 200 | 10 | Tipro | C |
| 52 | TPAOH | 1.0 | 35 | 5 | 14 | 1715 | 150 | 4 | DC | B |
| 53 | TPAOH | 1.0 | 35 | 5 | 14 | 1715 | 150 | 11 | DC | B |
| 54 | TPAOH | 1.0 | 35 | 5 | 14 | 1715 | 200 | 4 | DC | B |
| 55 | TPAOH | 1.0 | 35 | 5 | 14 | 1715 | 200 | 11 | DC | B |
| 56 | TPAOH | 1.0 | 35 | 5 | 14 | 1715 | 150 | 4 | ANF | A |
| 57 | TPAOH | 1.0 | 35 | 5 | 14 | 1715 | 150 | 10 | ANF | A |
| 58 | TPAOH | 1.0 | 35 | 5 | 14 | 1715 | 200 | 4 | ANF | A |
| 59 | TPAOH | 1.0 | 35 | 5 | 14 | 1715 | 200 | 10 | ANF | A |
| 60 | TPAOH | 1.0 | 35 | 5 | 14 | 1715 | 150 | 4 | ANF | B |
| 61 | TPAOH | 1.0 | 35 | 5 | 14 | 1715 | 150 | 10 | ANF | B |
| 62 | TPAOH | 1.0 | 35 | 5 | 14 | 1715 | 200 | 4 | ANF | B |
| 63 | TPAOH | 1.0 | 35 | 5 | 14 | 1715 | 200 | 10 | ANF | B |
| 64 | TPAOH | 1.0 | 35 | 5 | 10 | 1779 | 200 | 9 | AA | B |
| 65 | TEAOH | 1.0 | 15 | 5 | 14 | 1715 | 200 | 7 | Tipro | B |

TABLE I¹-continued

| 66 | TPAOH | 1.0 | 35 | 5 | 10 | 1779 | 200 | 10 | Tipro | B |

¹All amounts are given in moles. The value of "e" was 3.6.
²Seed crystals of silicalite were added after formation of the reaction mixture in examples 40 to 43 and examples 52 to 66. The seed crystals were present in an amount of five wt. percent of the solid oxides based on the weight of the reaction mixture, exclusive of the seed crystals.
³Kaiser alumina was employed in examples 44 to 51.

EXAMPLE 67

(a) Products from Examples 8, 37, 40 and 44 were calcined and treated as hereinafter described and were then employed to determine adsorption capacities of TASO-45. The adsorption capacities were measured using a standard McBain-Bakr gravimetric adsorption apparatus on samples activated in a vacuum at 350° C.

The data for TASO-45 as prepared in Examples 8, 37, 40 and 44 were as follows:

|  | Kinetic Diameter, Å | Pressure (Torr) | Temp (°C.) | Weight Percent Adsorbed* |
|---|---|---|---|---|
| (b) Example 8: | | | | |
| $O_2$ | 3.46 | 105 | −183 | 15.0 |
| $O_2$ | 3.46 | 741 | −183 | 18.7 |
| Cyclohexane | 6.0 | 65 | 23.6 | 4.9 |
| Neopentane | 6.2 | 739 | 23.5 | 2.0 |
| $H_2O$ | 2.65 | 4.6 | 23.8 | 6.6 |
| $H_2O$ | 2.65 | 20.0 | 24.0 | 13.1 |

*Calcined at 500° C. in air for 1.5 hours prior to activation.

| (c) Example 37: | | | | |
|---|---|---|---|---|
| $O_2$ | 3.46 | 106 | −183 | 12.1 |
| $O_2$ | 3.46 | 744 | −183 | 14.4 |
| Cyclohexane | 6.0 | 82 | 23.9 | 5.6 |
| Isobutane | 5.0 | 740 | 24.2 | 6.2 |
| Neopentane | 6.2 | 741 | 25.3 | 1.7 |
| $H_2O$ | 2.65 | 4.6 | 24.9 | 5.5 |
| $H_2O$ | 2.65 | 19.0 | 24.8 | 9.8 |

*Calcined at 600° C. in air for one hour prior to activation.

| (d) Example 40: | | | | |
|---|---|---|---|---|
| $O_2$ | 3.65 | 105 | −183 | 13.6 |
| $O_2$ | 3.65 | 747 | −183 | 17.7 |
| Cyclohexane | 6.0 | 71 | 23.5 | 7.3 |
| Neopentane | 6.2 | 750 | 23.5 | 2.7 |
| $H_2O$ | 2.65 | 4.6 | 23.5 | 7.7 |
| $H_2O$ | 2.65 | 19.0 | 23.4 | 15.5 |

*Calcined at 500° C. in air for one hour prior to activation.

| (e) Example 44: | | | | |
|---|---|---|---|---|
| $O_2$ | 3.65 | 105 | −183 | 16.7 |
| $O_2$ | 3.65 | 747 | −183 | 18.3 |
| Cyclohexane | 6.0 | 71 | 23.5 | 0.7 |
| Neopentane | 6.2 | 750 | 23.5 | 0.4 |
| $H_2O$ | 2.65 | 4.6 | 23.5 | 5.3 |
| $H_2O$ | 2.65 | 19.0 | 23.4 | 11.5 |

*Calcined at 500° C. in air for one hour prior to activation.

(f) From the data set forth in parts (b), (c), (d) and (e) it was determined that the pore size of TASO-45 is about 6.0Å.

EXAMPLE 68

(a) The as-synthesized products of Examples 8, 12, 29, 37, 40, 42, 44, 51 and 66 were analyzed (chemical analysis) to determine the weight percent $Al_2O_3$, $SiO_2$, $TiO_2$ LOI (Loss on Ignition), carbon (C) and nitrogen (N) present as a result of the template. The results of these analyses were as follows.

| (b) Example 8: | |
|---|---|
| Component | Weight Percent |
| $Al_2O_3$ | 2.83 |
| $SiO_2$ | 71.8 |
| $TiO_2$ | 11.3 |
| $Na_2O$ | 1.0 |
| C | 6.3 |
| N | 0.70 |
| LOI | 12.4 |

The above chemical analysis gives an anhydrous formula of:

0.044 R $(Al_{0.040}Si_{0.859}Ti_{0.101})$

| (c) Example 12: | |
|---|---|
| Component | Weight Percent |
| $Al_2O_3$ | 3.01 |
| $SiO_2$ | 74.1 |
| $TiO_2$ | 8.45 |
| $Na_2O$ | 1.08 |
| C | 6.5 |
| N | 0.70 |
| LOI | 12.0 |

The above chemical analysis gives an anhydrous formula of:

0.045 R $(Al_{0.042}Si_{0.882}Ti_{0.076})$

| (d) Example 29: | |
|---|---|
| Component | Weight Percent |
| $Al_2O_3$ | 3.7 |
| $SiO_2$ | 76.8 |
| $TiO_2$ | 6.2 |
| $Na_2O$ | 0.95 |
| C | 7.3 |
| N | 0.75 |
| LOI | 12.3 |

The above chemical analysis gives an anhydrous formula of:

0.053 R $(Al_{0.051}Si_{0.895}Ti_{0.055})$

| (e) Example 37: | |
|---|---|
| Component | Weight Percent |
| $Al_2O_3$ | 2.88 |
| $SiO_2$ | 67.0 |
| $TiO_2$ | 12.5 |
| $Na_2O$ | 4.34 |
| C | 4.7 |
| N | 0.44 |
| LOI | 12.8 |

The above chemical analysis gives an anhydrous formula of:

0.033 R (Al$_{0.043}$Si$_{0.839}$Ti$_{0.118}$)

(f) Example 40:

| Component | Weight Percent |
|---|---|
| Al$_2$O$_3$ | 2.8 |
| SiO$_2$ | 66.7 |
| TiO$_2$ | 12.3 |
| Na$_2$O | 3.3 |
| C | 5.5 |
| N | 0.58 |
| LOI | 14.5 |

The above chemical analysis gives an anhydrous formula of:

0.038 R (Al$_{0.042}$Si$_{0.842}$Ti$_{0.117}$)

(g) Example 42:

| Component | Weight Percent |
|---|---|
| Al$_2$O$_3$ | 2.6 |
| SiO$_2$ | 65.2 |
| TiO$_2$ | 10.7 |
| Na$_2$O | 6.2 |
| C | 4.6 |
| N | 0.48 |
| LOI | 14.3 |

The above chemical analysis gives an anhydrous formula of:

0.032 R (Al$_{0.040}$Si$_{0.854}$Ti$_{0.106}$)

(h) Example 44

| Component | Weight Percent |
|---|---|
| Al$_2$O$_3$ | 1.4 |
| SiO$_2$ | 80.3 |
| TiO$_2$ | 2.7 |
| Na$_2$O | 1.8 |
| C | 6.0 |
| N | 0.64 |
| LOI | 13.0 |

The above chemical analysis gives an anhydrous formula of:

0.042 R (Al$_{0.020}$Si$_{0.956}$Ti$_{0.024}$)

(i) Example 51

| Component | Weight Percent |
|---|---|
| Al$_2$O$_3$ | 1.5 |
| SiO$_2$ | 80.5 |
| TiO$_2$ | 3.2 |
| Na$_2$O | 1.7 |
| C | 6.7 |
| N | 0.59 |
| LOI | 12.7 |

The above chemical analysis gives an anhydrous formula of:

0.047 R (Al$_{0.021}$Si$_{0.951}$Ti$_{0.029}$)

(j) Example 66

| Component | Weight Percent |
|---|---|
| Al$_2$O$_3$ | 2.80 |
| SiO$_2$ | 73.1 |
| TiO$_2$ | 12.4 |
| Na$_2$O | 0.92 |
| C | 6.7 |
| N | 0.63 |
| LOI | 11.1 |

The above chemical analysis gives an anhydrous formula of:

0.047 R (Al$_{0.039}$Si$_{0.853}$Ti$_{0.109}$)

(k) EDAX (energy dispersive analysis by X-ray) microprobe analysis was carried out on clean crystals on the TASO-45 products prepared in Examples 8, 12 and 29, supra. The EDAX microprobe analysis showed that at least 7.1 weight percent titanium was present as an integral part of the crystal particles of each of the TASO-45 compositions. The relative amounts of SiO$_2$, Al$_2$O$_3$, and TiO$_2$, expressed as a relative weight percent was as follows:

| | Average of Spot Probes |
|---|---|
| | EXAMPLE 29 |
| Ti | 1.5 |
| Si | 9.7 |
| Al | 0.9 |
| | EXAMPLE 8 |
| Ti | 0.7 |
| Si | 10.0 |
| Al | 0.8 |
| | EXAMPLE 12 |
| Ti | 0.2 |
| Si | 10.0 |
| Al | 0.5 |

EXAMPLE 69

(a) TASO-45, as referred to in Example 12, was subjected to X-ray analysis. TASO-45 was determined to have a characteristic X-ray powder diffraction pattern which contains at least the d-spacings set forth in Table II, below:

TABLE II

| 2θ | d, (A) | 100 × I/Io |
|---|---|---|
| 7.9 | 11.17 | 59 |
| 8.8 | 10.03 | 37 |
| 11.9 | 7.46 | 9 |
| 12.5 | 7.10 | 4 |
| 13.2 | 6.71 | 4 |
| 13.9 | 6.38 | 9 |
| 14.7 | 6.02 | 9 |
| 15.5 | 5.72 | 6 |
| 15.9 | 5.58 | 8 |
| 17.2 | 5.14 | 3 |
| 17.7 | 5.01 | 5 |
| 19.2 | 4.62 | 5 |
| 20.0 | 4.45 | 2 |
| 20.3 | 4.37 | 9 |
| 20.8 | 4.27 | 9 |
| 22.2 | 4.01 | 5 |
| 23.1 | 3.85 | 100 |
| 23.7 | 3.76 | 34 |
| 23.9 | 3.73 | 44 |
| 24.4 | 3.66 | 26 |
| 25.8 | 3.448 | 9 |
| 26.9 | 3.314 | 8 |

TABLE II-continued

| 2Θ | d, (A) | 100 × I/Io |
|---|---|---|
| 27.4 | 3.258 | 3 |
| 29.2 | 3.057 | 9 |
| 29.9 | 2.989 | 12 |
| 30.3 | 2.951 | 5 |
| 32.7 | 2.738 | 3 |
| 34.4 | 2.609 | 3 |
| 34.8 | 2.576 | 2 |
| 35.7 | 2.517 | 3 |
| 36.0 | 2.495 | 6 |
| 37.2 | 2.418 | 2 |
| 37.4 | 2.407 | 3 |
| 37.5 | 2.400 | 3 |
| 45.0 | 2.015 | 7 |
| 45.2 | 2.005 | 9 |
| 46.4 | 1.956 | 2 |
| 47.4 | 1.919 | 3 |
| 48.5 | 1.876 | 4 |
| 48.7 | 1.871 | 2 |
| 51.8 | 1.766 | 2 |
| 54.6 | 1.680 | 2 |
| 55.0 | 1.671 | 3 |
| 55.2 | 1.664 | 3 |

(b) All of the as-synthesized TASO-45 compositions for which X-ray powder diffraction data have been obtained to date have patterns which are characterized by the data of table III, below.

TABLE III

| 2Θ | d, (A) | Relative Intensity |
|---|---|---|
| 7.9–8.0 | 11.17–11.10 | m-vs |
| 8.8–8.9 | 10.03–9.97 | m |
| 23.1–23.3 | 3.85–3.82 | m-vs |
| 23.7–23.8 | 3.76–3.75 | m |
| 23.9–24.0 | 3.73–3.71 | m |
| 24.4–24.5 | 3.66–3.63 | m |

(c) A portion of the as-synthesized TASO-45 of Example 11 was calcined in air at 500° C. for 1.5 hours. The calcined product was characterized by the X-ray powder diffraction pattern of Table IV, below:

TABLE IV

| 2Θ | d, (A) | 100 × I/Io |
|---|---|---|
| 8.0 | 11.10 | 100 |
| 8.9 | 9.97 | 59 |
| 11.9 | 7.46 | 4 |
| 13.3 | 6.68 | 4 |
| 14.0 | 6.34 | 11 |
| 14.9 | 5.97 | 13 |
| 15.6 | 5.69 | 8 |
| 16.0 | 5.56 | 10 |
| 17.8 | 4.97 | 6 |
| 19.3 | 4.60 | 4 |
| 20.4 | 4.36 | 5 |
| 20.9 | 4.25 | 8 |
| 22.3 | 3.99 | 4 |
| 23.2 | 3.84 | 62 |
| 23.3 | 3.82 | 59 |
| 23.8 | 3.75 | 24 |
| 24.0 | 3.71 | 32 |
| 24.4 | 3.66 | 21 |
| 25.7 | 3.474 | 3 |
| 25.9 | 3.438 | 4 |
| 26.7 | 3.334 | 4 |
| 29.3 | 3.048 | 7 |
| 29.9 | 2.989 | 9 |
| 30.4 | 2.943 | 5 |
| 32.8 | 2.731 | 3 |
| 36.1 | 2.487 | 4 |
| 37.5 | 2.400 | 3 |
| 45.1 | 2.010 | 5 |
| 45.6 | 1.991 | 8 |
| 48.6 | 1.873 | 4 |
| 48.8 | 1.868 | 3 |

TABLE IV-continued

| 2Θ | d, (A) | 100 × I/Io |
|---|---|---|
| 53.5 | 1.713 | 5 |

(d) All of the as-synthesized and calcined TASO-45 compositions for which X-ray powder diffraction data have been obtained to date have patterns which are characterized by the data of Table V, below.

TABLE V

| 2Θ | d, (A) | 100 × I/Io |
|---|---|---|
| 7.9–8.0 | 11.17–11.10 | 36–100 |
| 8.8–8.9 | 10.03–9.97 | 25–60 |
| 9.0–9.1 | 9.83–9.72 | 14–18 |
| 11.8–12.0 | 7.50–7.38 | 2–11 |
| 12.5–12.6 | 7.10–7.03 | 3–6 |
| 13.2–13.3 | 6.71–6.68 | 4–7 |
| 13.9–14.0 | 6.38–6.34 | 6–12 |
| 14.7–14.9 | 6.02–5.97 | 7–16 |
| 15.5–15.6 | 5.72–5.69 | 6–12 |
| 15.9–16.0 | 5.58–5.56 | 6–14 |
| 16.5–16.6 | 5.37–5.34 | 2–3 |
| 17.2–17.3 | 5.14–5.13 | 2–5 |
| 17.7–17.8 | 5.01–4.97 | 4–6 |
| 19.2–19.3 | 4.62–4.60 | 4–8 |
| 19.9–20.0 | 4.46–4.45 | 2–3 |
| 20.3–20.5 | 4.37–4.33 | 5–9 |
| 20.8–21.0 | 4.27–4.23 | 8–13 |
| 21.7–21.8 | 4.10–4.08 | 1–3 |
| 22.1–22.3 | 4.02–3.99 | 3–7 |
| 23.1–23.3 | 3.85–3.82 | 62–100 |
| 23.7–23.8 | 3.76–3.75 | 24–34 |
| 23.9–24.0 | 3.73–3.71 | 32–50 |
| 24.4–24.5 | 3.66–3.63 | 21–31 |
| 25.4–25.7 | 3.507–3.474 | 3–5 |
| 25.7–26.0 | 3.474–3.427 | 3–9 |
| 26.3–26.7 | 3.389–3.334 | sh-8 |
| 26.7–27.1 | 3.339–3.290 | 4–16 |
| 27.3–27.7 | 3.267–3.220 | 3–8 |
| 28.0–28.4 | 3.187–3.143 | 2–3 |
| 29.9–29.4 | 3.057–3.039 | 7–10 |
| 29.9–30.1 | 2.989–2.969 | 9–16 |
| 30.3–30.4 | 2.951–2.943 | 5–6 |
| 32.7–32.8 | 2.738–2.731 | 3–4 |
| 34.3–34.6 | 2.614–2.592 | 3–7 |
| 34.6–35.0 | 2.592–2.564 | 2–3 |
| 35.6–35.8 | 2.522–2.508 | 2–4 |
| 36.0–26.3 | 2.495–2.475 | 3–9 |
| 37.1–27.3 | 2.423–2.411 | 2–3 |
| 37.4–37.7 | 2.407–2.386 | 3–5 |
| 41.3–41.5 | 2.186–2.176 | 2–3 |
| 45.0–45.2 | 2.015–2.005 | 5–9 |
| 45.3–45.6 | 2.002–1.991 | 6–11 |
| 46.4–46.5 | 1.956–1.953 | 2–3 |
| 47.3–47.6 | 1.922–1.910 | 2–3 |
| 48.4–48.6 | 1.881–1.873 | 3–4 |
| 48.7–48.8 | 1.871–1.868 | 2–3 |
| 51.8–52.0 | 1.766–1.759 | 1–3 |
| 53.5 | 1.713 | 5 |
| 54.4–54.7 | 1.687–1.678 | 2–3 |
| 54.9–55.1 | 1.672–1.667 | 3–5 |
| 55.2–55.5 | 1.664–1.656 | 3–4 |

EXAMPLE 70

In order to demonstrate the catalytic activity of the TASO-45 calcined samples of the products of Examples 8, 29 and 37 wee then tested for catalytic cracking. The test procedure employed was the catalytic cracking of premixed two (2) mole percent n-butane in helium stream in a ½ O.D. quartz tube reactor up to about 5 grams (20–40 mesh) of the TASO-45 sample to be tested. The sample was activated in situ for 60 minutes at 500° C. under 200 cm$^3$/min dry helium purge. Then the two (2) mole (percent) n-butane in helium at a flow rate of 50 cm$^3$/min was passed over the sample for 40 minutes with product stream analysis being carried out at 10 minute intervals. The pseudo-first-order rate constant ($k^4$) was then calculated to determine the catalytic activity of the TASO-45 composition. The $k^4$ value cm³/g min) obtained for the TASO-45 compositions are set forth below.

| Sample | Rate Constant ($k^4$) |
|---|---|
| Ex. 8 | 5.6 |
| Ex. 29 | 16.8 |
| Ex. 37 | 0.2 |

EXAMPLE 71

This is a comparative example wherein Example 1 of European Patent Application No. 82109451.3 was repeated and the product evaluated by several techniques as hereinafter discussed:

(a) Example 1 of European Patent Application No. 82109451.3 was repeated with the starting reaction mixture having a composition based on molar ratios of:

1 $Al_2O_3$: 47 $SiO_2$: 1.32 $TiO_2$: 11.7 NaOH: 28 TPAOH: 1498$H_2O$

The reaction mixture was divided and placed in two digestion vessels. At the end of the procedure set forth in Example 1 of the European application a sample of the product from each digestion vessel was analyzed and gave the following chemical analyses.

| | Weight Percent | |
|---|---|---|
| | Sample 1 | Sample 2 |
| $SiO_2$ | 75.3 | 75.9 |
| $Al_2O_3$ | 3.02 | 2.58 |
| $TiO_2$ | 3.91 | 4.16 |
| $Na_2O$ | 3.66 | 3.46 |
| C | 6.3 | 6.7 |
| N | 0.62 | 0.65 |
| LOI | 14.0 | 14.0 |

The two samples were then analyzed by SEM (scanning electron microscope) and EDAX (energy dispersive analysis by X-ray) microprobe. The SEM probe of the two samples showed four morphologies to be present versus a single morphology for TASO-45 crystals. The four morphologies of the two samples prepared in accordance with the aforementioned European application and the EDAX microprobe analysis for each were as follows:

(1) Smooth, intergrown hexagonal particles which are associated with a ZSM-5 morphology had an EDAX microprobe of:

| | Average of Spot Probes |
|---|---|
| Ti | 0 |
| Si | 1.0 |
| Al | 0.05 |

(2) Flat, smooth plates had an EDAX microprobe of:

| | Average of Spot Probes |
|---|---|
| Ti | 0.13 |
| Si | 1.0 |
| Al | 0.05 |

(3) Sphere and elongated bundles had an EDAX microprobe of:

| | Average of Spot Probes |
|---|---|
| Ti | 0.22 |
| Si | 1.0 |
| Al | 0.05 |
| Na | 0.10 |

(4) Needles of fine rods had an EDAX microprobe of:

| | Average of Spot Probes |
|---|---|
| Ti | 0.05 |
| Si | 0.8 |
| Al | 0.13 |
| Na | 0.05 |
| Cl | 0.10 |

The above SEM and EDAX data demonstrate that although ZSM-5 type crystals were formed that these crystals contained no detectable titanium. The only detectable titanium was present as impurity phases and not in crystals having the characteristic X-ray diffraction pattern of ZSM-5.

The X-ray diffraction patterns of the as-synthesized materials were obtained and the following X-ray patterns were observed:

TABLE VI

| (Sample 1) | |
|---|---|
| 2θ | d(Å) |
| 5.577 | 15.8467 |
| 5.950 | 14.8540 |
| 6.041 | 14.6293 |
| 6.535 | 13.5251 |
| 7.154 | 12.3567 |
| 7.895 | 11.1978 |
| 8.798 | 10.0504 |
| 9.028 | 9.7946 |
| 9.784 | 9.0401 |
| 11.846 | 7.4708 |
| 12.453 | 7.1079 |
| 12.725 | 6.9565 |
| 13.161 | 6.7267 |
| 13.875 | 6.3821 |
| 14.637 | 6.0518 |
| 14.710 | 6.0219 |
| 15.461 | 5.7310 |
| 15.881 | 5.5802 |
| 16.471 | 5.3818 |
| 17.218 | 5.1498 |
| 17.695 | 5.0120 |
| 19.212 | 4.6198 |
| 19.898 | 4.4619 |
| 20.045 | 4.4295 |
| 20.288 | 4.3770 |
| 20.806 | 4.2692 |
| 21.681 | 4.0988 |
| 22.143 | 4.0145 |
| 23.091 | 3.8516 |
| 23.641 | 3.7632 |
| 23.879 | 3.7263 |
| 24.346 | 3.6559 |
| 24.649 | 3.6116 |
| 25.548 | 3.4865 |
| 25.828 | 3.4494 |
| 26.228 | 3.3976 |
| 26.608 | 3.3501 |

TABLE VI-continued (Sample 1)

| 2Θ | d(Å) |
|---|---|
| 26.887 | 3.3158 |
| 27.442 | 3.2524 |
| 28.048 | 3.1812 |
| 28.356 | 3.1473 |
| 29.191 | 3.0592 |
| 29.912 | 2.9870 |
| 30.295 | 2.9502 |
| 32.736 | 2.7356 |
| 33.362 | 2.6857 |
| 34.355 | 2.6102 |
| 34.640 | 2.5894 |
| 34.887 | 2.5716 |
| 35.152 | 2.5529 |
| 35.551 | 2.5252 |
| 35.660 | 2.5177 |
| 36.031 | 2.4926 |
| 37.193 | 2.4174 |
| 37.493 | 2.3987 |
| 45.066 | 2.0116 |
| 45.378 | 1.9985 |
| 46.514 | 1.9523 |
| 47.393 | 1.9182 |

TABLE VII (Sample 2)

| 2Θ | d(Å) |
|---|---|
| 5.801 | 15.2353 |
| 6.012 | 14.7012 |
| 6.169 | 14.3265 |
| 7.970 | 11.0926 |
| 8.875 | 9.9636 |
| 9.118 | 9.6981 |
| 9.879 | 8.9532 |
| 11.933 | 7.4163 |
| 12.537 | 7.0605 |
| 12.808 | 6.9115 |
| 13.242 | 6.6860 |
| 13.957 | 6.3452 |
| 14.718 | 6.0186 |
| 14.810 | 5.9813 |
| 15.542 | 5.7014 |
| 15.954 | 5.5551 |
| 16.563 | 5.3521 |
| 17.316 | 5.1211 |
| 17.788 | 4.9862 |
| 19.291 | 4.6009 |
| 20.119 | 4.4134 |
| 20.382 | 4.3571 |
| 20.879 | 4.2544 |
| 21.735 | 4.0887 |
| 22.220 | 4.0007 |
| 23.170 | 3.8387 |
| 23.730 | 3.7494 |
| 23.964 | 3.7133 |
| 24.425 | 3.6442 |
| 24.722 | 3.6011 |
| 25.900 | 3.4399 |
| 26.734 | 3.3345 |
| 26.979 | 3.3047 |
| 27.251 | 3.2724 |
| 27.494 | 3.2440 |
| 28.175 | 3.1671 |
| 28.450 | 3.1371 |
| 29.287 | 3.0493 |
| 29.970 | 2.9814 |
| 30.371 | 2.9430 |
| 30.694 | 2.9127 |
| 31.312 | 2.8566 |
| 32.825 | 2.7283 |
| 33.457 | 2.6782 |
| 34.426 | 2.6051 |
| 34.723 | 2.5834 |
| 34.879 | 2.5722 |
| 35.709 | 2.5143 |
| 36.125 | 2.4863 |
| 37.248 | 2.4139 |
| 37.490 | 2.3988 |

TABLE VII-continued (Sample 2)

| 2Θ | d(Å) |
|---|---|
| 45.156 | 2.0078 |
| 45.453 | 1.9954 |
| 46.462 | 1.9544 |
| 46.608 | 1.9486 |

Tables VI and VII show an X-ray pattern typical of a ZSM-5 type product and can be attributed to the smooth, intergrown hexagonal particles which contained no titanium. The X-ray patterns of Tables VI and VII show three peaks (2Θ = 5.6–5.8, 12.45–12.54 and 24.5–24.72) which could not be explained. The two samples were calcined according to the conditions set forth in the European application with a portion of both samples being calcined at 540° C. for sixteen hours. The X-ray patterns of the calcined samples were as follows.

TABLE VIII (Sample 1)

| 2Θ | d(Å) |
|---|---|
| 6.141 | 14.3908 |
| 6.255 | 14.1303 |
| 8.011 | 11.0355 |
| 8.913 | 9.9209 |
| 9.144 | 9.6705 |
| 9.930 | 8.9068 |
| 11.979 | 7.3876 |
| 12.440 | 7.1152 |
| 13.289 | 6.6625 |
| 14.007 | 6.3224 |
| 14.874 | 5.9557 |
| 15.613 | 5.6757 |
| 15.995 | 5.5408 |
| 16.609 | 5.3373 |
| 17.353 | 5.1103 |
| 17.884 | 4.9597 |
| 19.335 | 4.5905 |
| 20.177 | 4.4008 |
| 20.463 | 4.3401 |
| 20.940 | 4.2422 |
| 21.845 | 4.0685 |
| 22.291 | 3.9880 |
| 23.186 | 3.8361 |
| 23.362 | 3.8076 |
| 23.817 | 3.7359 |
| 24.031 | 3.7031 |
| 24.510 | 3.6317 |
| 24.908 | 3.5747 |
| 25.699 | 3.4664 |
| 25.969 | 3.4309 |
| 26.371 | 3.3796 |
| 26.698 | 3.3389 |
| 27.022 | 3.2996 |
| 27.487 | 3.2449 |
| 28.184 | 3.1662 |
| 28.513 | 3.1303 |
| 29.369 | 3.0411 |
| 30.017 | 2.9769 |
| 30.468 | 2.9338 |
| 31.333 | 2.8548 |
| 32.877 | 2.7241 |
| 34.490 | 2.6003 |
| 35.062 | 2.5592 |
| 35.800 | 2.5082 |
| 36.186 | 2.4823 |
| 37.324 | 2.4092 |
| 37.654 | 2.3888 |
| 45.195 | 2.0062 |
| 45.631 | 1.9880 |
| 46.639 | 1.9474 |
| 47.547 | 1.9123 |
| 48.765 | 1.8674 |

TABLE IX
(Sample 2)

| 2Θ | d(Å) |
|---|---|
| 6.092 | 14.5084 |
| 6.295 | 14.0403 |
| 7.941 | 11.1328 |
| 8.838 | 10.0054 |
| 9.857 | 8.9730 |
| 11.921 | 7.4236 |
| 12.399 | 7.1383 |
| 13.222 | 6.6959 |
| 13.937 | 6.3539 |
| 14.811 | 5.9809 |
| 15.535 | 5.7038 |
| 15.916 | 5.5681 |
| 16.532 | 5.3620 |
| 17.262 | 5.1370 |
| 17.806 | 4.9811 |
| 19.268 | 4.6064 |
| 20.107 | 4.4160 |
| 20.389 | 4.3556 |
| 20.868 | 4.2567 |
| 21.807 | 4.0754 |
| 22.197 | 4.0047 |
| 23.116 | 3.8476 |
| 23.263 | 3.8235 |
| 23.755 | 3.7455 |
| 23.955 | 3.7147 |
| 24.432 | 3.6433 |
| 24.854 | 3.5823 |
| 25.653 | 3.4725 |
| 25.901 | 3.4398 |
| 26.265 | 3.3929 |
| 26.648 | 3.3451 |
| 26.976 | 3.3052 |
| 27.386 | 3.2566 |
| 28.156 | 3.1692 |
| 28.495 | 3.1323 |
| 29.304 | 3.0476 |
| 29.969 | 2.9815 |
| 30.384 | 2.9417 |
| 31.283 | 2.8592 |
| 32.819 | 2.7289 |
| 34.423 | 2.6052 |
| 34.993 | 2.5641 |
| 35.716 | 2.5138 |
| 36.146 | 2.4850 |
| 37.295 | 2.4110 |
| 37.562 | 2.3944 |
| 45.137 | 2.0086 |
| 45.523 | 1.9925 |
| 46.562 | 1.9504 |
| 47.509 | 1.9137 |

The X-ray diffraction patterns of the calcined samples show a ZSM-5 type pattern with only slight differences from the as-synthesized. When chemical analysis (bulk) of a portion of the calcined samples 1 and 2 are carried out, the following is obtained:

| | Weight Percent | |
|---|---|---|
| | Sample 1 | Sample 2 |
| $SiO_2$ | 79.6 | 81.2 |
| $Al_2O_3$ | 3.5 | 2.9 |
| $Na_2O$ | 4.4 | 4.1 |
| $TiO_2$ | 4.4 | 4.6 |
| Carbon | 0.11 | 0.10 |
| LOI* | 8.1 | 7.6 |

*Loss on Ignition

When the molar ratio of oxides is computed for the above bulk analysis the following is obtained:

1 $SiO_2$: 0.043 $TiO_2$: 0.021 $Al_2O_3$: 0.049 $Na_2O$

This compares quite well with the bulk chemical analysis reported in the European application which is:

1 $SiO_2$: 0.047 $TiO_2$: 0.023 $Al_2O_3$: 0.051 $Na_2O$

Although it is clear that the product crystals which gave the product an X-ray pattern characteristic of ZSM-5 contained no titanium, the bulk analysis of the product shows titanium to be present from crystals which do not have an X-ray diffraction pattern characteristic of ZSM-5.

EXAMPLE 72

This is a comparative example in which Example 8 of U.S. Pat. No. 4,410,501 was repeated and the product analyzed by several techniques.

A 2 liter beaker was placed on a stirring hotplate to which there were added 414.5 mL of distilled water. Titanium ethoxide, 26.55 gm, was added to the distilled $H_2O$ while stirring. A white gelatinous precipitate/suspension formed. The above suspension was cooled in an ice bath to 5° C. at which time 318.6 mL of a separately cooled 30% solution of $H_2O_2$ was added at a moderate rate. The slurry turned orange with the suspension/precipitate still present. The temperature was maintained at 5° C. for two hours with occasional stirring. The precipitate gradually dissolved and the solution became clear orange. A pre-cooled (5° C.) solution of 22.4% TPA-OH was added with moderate stirring and at a moderate rate to the titanium containing solution. The solution changed from orange to yellow. The solution was stirred at 5° C. for 1 hour, with the solution effervescing the entire time.

Separately, 1.042 gm $NaAlO_2$ were added to 84.89 gm Ludox-AS40 with stirring. The aluminate dissolved slowly. The $NaAlO_2$/Ludox solution was added to the yellow titanium containing solution. The entire mix became translucent yellow. The mixture was covered with a watch glass, removed from the ice bath and allowed to stand at room temperature overnight. Effervescence continued, even until the next morning. The covered solution was heated to 75° C. At about 65°, the solution became cloudy and thickened, but as the temperature increased, the solution became clearer. The solution was heated at 75° C. for 7 hours, then loaded into a 2 liter reactor and heated to 175° C. for 10 days. On cooling, the crystals were separated from the liquid phase and the crystals were washed thoroughly with hot distilled water. This sample was identified as sample TA.

The X-ray powder pattern of sample TA was obtained and was characteristic of a well crystallized MFI type zeolite, i.e., ZSM-5 or silicalite. The pattern also showed several additional peaks at 25.3°, 47.9° and 54.9° 2Θ which are indicative of crystalline $TiO_2$, anatase phase.

The chemical analysis of sample TA is shown in the following Table:

| | |
|---|---|
| $(TPA)_2O$, wt. %: | 9.13 |
| $SiO_2$, wt. %: | 79.70 |
| $Al_2O_3$, wt. %: | 1.30 |
| $TiO_2$, wt. %: | 6.03 |
| $SiO_2/Al_2O_3$: | 103.73 |
| Cation Equivalent, M+/Al: | 1.60 |

The data show the incorporation of a substantial amount of $TiO_2$ into the product composition with a small amount of $Al_2O_3$ as well.

The infrared spectrum of sample TA was also obtained and showed absorption bands at about 620 cm$^{-1}$, 760 cm$^{-1}$ and 985 cm$^{-1}$. In the above referenced U.S. Pat. No. 4,410,501, Taramasso reports a band at about 950 cm$^{-1}$ which he attributes to $Ti^{+4}$ in tetrahedral coordination with $Si^{+4}$. In Taramasso's subsequent publication with Perego et al., "Titanium-Silicalite: A Novel Derivative in the Pentasil Family", in "New Developments in Zeolite Science and Technology", Proceedings of the 7th International Zeolite Conference, Tokyo, August 17-22, 1986, Murakami et al. eds.., pp. 129-136, he states on pg. 132, that the infrared absorption band is located at 970 cm$^{-1}$. Inspection of the spectra presented in the '501 patent does indeed suggest that the band is located at about 970 cm$^{-1}$, and not at the lower frequency as suggested by Taramasso in column 2, lines 38-41 of the '501 patent.

In a recent report by Kornatowski et al., "Growth of Large Crystals of Titanium Molecular Sieve of ZSM-5 Structure, Presented at the 8th International Zeolite Conference, Amsterdam, July 10-14, 1989, the 970 cm$^{-1}$ band assignment is attributed to extra framework $TiO_2$ species, "contrary to Taramasso". Both the Taramasso and the Perego references rely on the report of Best and Condrate, "A Raman study of $TiO_2$—$SiO_2$ Glasses Prepared by Sol-Gel Processes", J. Mat. Sci. Leters 4 (1985), 994-98 which reports on the Raman spectra of $TiO_2$—$SiO_2$ glasses. They suggest a band at about 950 cm$^{-1}$ which they attribute to tetrahedrally coordinated titanium in glasses containing very small quantities of titanium. The Best et al. paper supports the premise that the 620 cm$^{-1}$ and 760 cm$^{-1}$ bands at least are due to the presence of anatase $TiO_2$ and that the 985 cm$^{-1}$ band is indeed, extra framework $TiO_2$ in transition from the glass phase to anatase, and not to titanium in tetrahedral coordination with silicon. Thus, none of the infrared bands observed for the TA sample is attributable to tetrahedrally coordinated titanium.

SEM and EDAX examination of sample TA showed crystals of several morphologies. The bulk of the crystals were spherulitic aggregates or agglomerates, with some rod shaped crystals present. The rod shaped morphology could be attributable to a silicalite type phase-no aluminum in the MFI framework, while the spherulitic aggregates are typical of the ZSM-5 morphology-MFI framework containing aluminum. There was some debris observed with no regular morphology. In addition, the crystals appeared to have debris covering their surfaces as well. EDAX showed the presence of a small amount of titanium throughout the entire sample. There were however, substantially higher levels of Ti in areas heavy in debris. Since the spot probe of the EDAX covers areas substantially greater than the crystal sizes under observation, Analytical Transmission Electron Microscopy was used to analyze smaller areas of the crystals. The ATEM measures an area of 200 square Angstroms, rather than the approximately four square micron areas measured by the spot probe of the SEM.

ATEM examination was performed on the product by two methods. The first, the "dry brush" method looks only at the outside surfaces of the material under observation. The other method uses a microtome method to prepare thin slices of the material, thus allowing the observation and analysis of the interior portions of the material. In the dry brush method, both crystal morphologies were examined, as was the debris. Spot probe analysis of the debris showed that this particle is $TiO_2$. Spot probe analysis of the rod-like crystals (morphology of silicalite) showed a small amount of titanium and nearly no aluminum. The rods have a surface coating of debris. Crystals with a ZSM-5 type morphology were also analyzed. Aluminum is present in these crystals, but the level of titanium is very low. Again these crystals were covered debris. Microtome analysis of thin sections of the crystals gave the same results as the dry brush method. That is, the silicalite rod-like crystal showed very little titanium and no aluminum while the ZSM-5 type crystals show the presence of aluminum, but the titanium is barely detectable.

The SEM and EDAX data show that the titanium introduced into the synthesis gel, precipitated, as the aqueous chemistry at this high pH would predict, and crystallized as the anatase phase of $TiO_2$, depositing on the filter cake with the zeolite crystals and coating the crystals with some of the tinier, non-agglomerated $TiO_2$ phases.

The data obtained from the extensive analysis of sample TA shows that there is no valid reason to conclude that Ti, present in the bulk analysis of the solid, is present in the framework of the zeolite. The material contains greater than 6 wt. % $TiO_2$; most of it can be accounted for by the presence of anatase in the X-ray powder pattern. Another small fraction can be observed coating the surface of the zeolite crystals. These small particles are too small to be observed in the X-ray powder pattern. The Analytical TEM show consistently, that the outside surface of the crystals "dry brush" samples) contain more Ti than the interior portions of the crystal (microtome sections). The fact that a barely detectable amount of Ti is found inside the crystals can be accounted for by several reasons, without invoking substitution in the framework. The Ti could very well be left on the surface of the crystal by the very technique that allows us to observe the interior portions of the crystal, the microtome technique. A more likely source is the presence of an extraneous or extra framework titanium containing species.

PROCESS APPLICATIONS

The TASO-45 compositions of this invention have unique surface characteristics making them useful as molecular sieves and as catalysts or as bases for catalysts in a variety of separation, hydrocarbon conversion and oxidative combustion processes. The TASO-45 compositions can be impregnated or otherwise associated with catalytically active metals by the numerous methods known in the art and used, for example, in fabricating catalysts compositions containing alumina or aluminosilicate materials.

One use of the crystalline materials of this invention is to separate mixtures of molecular species. Prior to use in a separation process, the TASO-45 materials are activated to remove at least some of any molecular species, e.g., templating agent, which may be present in the intracrystalline pore system as a result of synthesis. This may be accomplished as described above, i.e., by heating.

The crystalline materials of this invention are capable of separating mixtures of molecular species based on the molecular size (kinetic diameters) or on the degree of polarity of the molecular species. When the separation of molecular species is based on molecular size, the crystalline microporous material is chosen in view of the dimensions of its pores such that at least the smallest molecular specie of the mixture can enter the intracrystalline void space while at least the largest specie is excluded. The kinetic diameters of various molecules such as oxygen, nitrogen, carbon dioxide, carbon monoxide are provided in D. W. Breck, ZEOLITE MOLECULAR SIEVES, John Wiley and Sons (1974) p. 636.

When the separation is based on degree of polarity, it is generally the case that the mildly hydrophobic crystalline material of this invention will preferentially adsorb the less polar molecular species of a mixture having different degrees of polarity even though both molecular species can communicate with the pore system of the crystalline material. For example, hydrocarbons such as paraffins, olefins, etc., which are less polar, will be preferentially adsorbed over water.

If one of the molecular species is a small impurity, the separation may be effected in the conventional manner by simply passing the stream to be treated through a bed of the particular crystalline material desired. As the operation of the process continues, there develops in the bed a so-called "front" between the material loaded with the impurity and the material not so loaded. This front moves through the bed in the direction of gas flow. Before the front reaches the downstream end of the bed, the bed is regenerated by cutting off the flow of feed stream and passing through the bed a purge gas which (usually at a temperature of about 50°–150° C.) desorbs the impurity from the bed. If the purge gas is adsorbed on the bed, this gas can be removed by passing one or two bed volumes of the feed stream through the bed.

If the concentration of one of the species in the mixture is large, e.g., several percents, other conventional techniques, such as pressure swing adsorption (PSA) and thermal swing adsorption may be used. Such techniques are well known to those skilled in the separation art. See, e.g., U.S. Pat. Nos. 4,723,966, 4,589,888, and 4,398,926. For example, a pressure swing adsorption process will operate at a temperature and pressure sufficient to effect the adsorption and desorption of the component or molecular specie which one wants to remove. Typically the temperature is preferably maintained in the range of about −50° to 100° C. and preferably from about 0° to 50° C. The pressure during adsorption can vary from about 0.2 psia (1.4 kPa) to about 1500 psia (10,342 kPa), preferably from about 50 psia (344 kPa) to about 500 psia (3,447 kPa) and more preferably from about 75 psia (517 kPa) to about 350 psia (2,413 kPa). The pressure during desorption is lower than during adsorption and effective to cause desorption of the adsorbed component. The range of this pressure is from about 0.1 torr (1.3 Pa) to 150 psia (1,034 kPa), preferably from about 0.1 torr (1.3 Pa) to 15 psia (103 kPa) and more preferably from about 0.1 torr (1.3 Pa) to about 250 torr (333 Pa). The cyclic process can comprise additional adsorption and regeneration steps as well as intermediate depressurization and purging steps.

The hydrocarbon conversion reactions catalyzed by TASO-45 compositions include: cracking; polymerization; reforming; hydrogenation; dehydrogenation; and hydration.

TASO-45 containing catalyst compositions may be employed in reforming processes in which the hydrocarbon feedstocks contact the catalyst at temperatures between about 700° F. and about 1000° F., hydrogen pressures of between about 100 and about 500 p.s.i.g., LHSV values in the range between about 0.1 and about 10 and hydrogen to hydrocarbon molar ratios in the range between about 1 and about 20, preferably between about 4 and about 12.

Further, TASO-45 containing catalysts which contain hydrogenation promoters, are useful in hydroisomerization processes wherein the feedstock(s), such as normal paraffins, is converted to saturated branched-chain isomers. Hydroisomerization processes are typically carried out at a temperature between about 200° F. and about 600° F., preferably between about 300° F. and about 550° F. with an LHSV value between about 0.2 and about 1.0. Hydrogen is typically supplied to the reactor in admixture with the hydrocarbon feedstock in molar proportions of hydrogen to the feedstock of between about 1 and about 5.

TASO-45-containing compositions similar to those employed for hydroisomerization may also be employed at between about 650° F. and about 1000° F., preferably between about 850° F. and about 950° F. and usually at somewhat lower pressures within the range between about 15 and about 50 p.s.i.g. for the hydroisomerization of normal paraffins. Preferably the paraffin feedstock comprises normal paraffins having a carbon number range of $C_7$–$C_{20}$. The contact time between the feedstock and the TASO-45 containing catalyst is generally relatively short to avoid undesirable side reactions such as olefin polymerization and paraffin cracking. LHSV values in the range between about 0.1 and about 10, preferably between about 1.0 and about 6.0 are suitable.

TASO-45 containing catalysts may be employed in catalytic cracking processes wherein such are preferably employed with feedstocks such as gas oils, heavy naphthas, deasphalted crude oil residues, etc. with gasoline being the principal desired product. Temperature conditions are typically between about 850° and about 1100° F., LHSV values between about 0.5 and about 10 pressure conditions are between about 0 p.s.i.g. and about 50 p.s.i.g.

TASO-45 containing catalysts may be employed for dehydrocyclization reactions which employ paraffinic hydrocarbon feedstocks, preferably normal paraffins having more than 6 carbon atoms, to form benzene, xylenes, toluene and the like. Dehydrocyclization processes are typically carried out using reaction conditions similar to those employed for reforming. For such processes it is preferred to use a Group VIII non-noble metal cation such as platinum in conjunction with the TASO-45 composition.

TASO-45 containing catalysts may be used in catalytic hydrofining wherein the primary objective is to provide for the selective hydrodecomposition of organic sulfur and/or nitrogen compounds without substantially affecting hydrocarbon molecules present therewith. For this purpose it is preferred to employ typical hydrotreating conditions. The catalysts are the same typically of the same general nature as described in connection with dehydrocyclization operations. Feedstocks commonly employed for catalytic hydroforming include: gasoline fractions; kerosenes; jet fuel fractions; diesel fractions; light and heavy gas oils; deasphalted crude oil residua; and the like. The feedstock may contain up to about 5 weight percent of sulfur and up to about 3 weight percent of nitrogen.

TASO-45 containing catalysts may be employed for isomerization processes under conditions similar to those described above for reforming although isomerization processes tend to require somewhat more acidic catalysts than those employed in reforming processes. Olefins are preferably isomerized at temperatures between about 500° F. and about 900° F., while paraffins, naphthenes and alkylaromatics are isomerized at temperatures of 700°-1000° F. Particularly desirable isomerization reactions contemplated herein include the conversion of n-heptane and/or n-octane to isoheptanes, iso-octanes, butane to iso-butane, methylcyclopentane to cyclohexane, 1-butene to 2-butene and/or isobutene, n-hexene to isohexane, cyclohexane to methylcyclopentene, etc. The preferred cation form is a combination of a TASO-45 with polyvalent metal compounds (such as sulfides) of metals of Group II-A, Group II-B and rare earth metals.

The TASO-45 compositions of this invention may be employed in conventional molecular sieve processes as heretofore have been carried out using aluminosilicate, aluminophosphate or other commonly employed molecular sieves. TASO-45 compositions are preferably activated prior to their use in a molecular sieve process to remove any molecular species which may be present in the intracrystalline pore system as a result of synthesis or otherwise. For the TASO-45 compositions this is sometimes accomplished by thermally destroying the organic species present in an as-synthesized TASO-45 since such organic species may be too large to be desorbed by conventional means.

We claim as our invention:

1. A crystalline molecular sieve having a three-dimensional microporous framework structure of $TiO_2$, $AlO_2$ and $SiO_2$ tetrahedral units, having an intracrystalline pore system where the pores have nominal diameters of about 6 Angstroms and having a chemical composition on an anhydrous basis expressed by the formula:

$$mR: (Ti_xAl_ySi_z)O_2$$

where "R" represents at least one organic templating agent present in the intracrystalline pore system; "m" represents the moles of "R" present per mole of $(Ti_xAl_ySi_z)O_2$ and has a value from zero to about 0.3; and "x", "y", and "z" represent the mole fractions of titanium, aluminum, and silicon, respectively, present as tetrahedral oxides, said mole fractions being such that they are within the compositional area defined by points A, B, C, and D of the ternary diagram of FIG. 1 and having a characteristic X-ray pattern as set forth in Table III

TABLE III

| 2θ | d, (Å) | Relative Intensity |
|---|---|---|
| 7.9–8.0 | 11.17–11.10 | m-vs |
| 8.8–8.9 | 10.03–9.97 | m |
| 23.1–23.3 | 3.85–3.82 | m-vs |
| 23.7–23.8 | 3.76–3.75 | m |
| 23.9–24.0 | 3.73–3.71 | m |
| 24.4–24.5 | 3.66–3.63 | m. |

2. The crystalline molecular sieve of claim 1 where the mole fractions of titanium, aluminum and silicon are within the compositional area defined by points f, g, h and i of the ternary diagram of FIG. 2.

3. The crystalline molecular sieve of claim 1 where the mole fractions of titanium, aluminum and silicon are within the compositional area defined by points a, b and c of the ternary diagram of FIG. 3.

4. The crystalline molecular sieve of claim 1 where the mole fractions of titanium, aluminum and silicon are within the compositional area defined by points c, d and e of the ternary diagram of FIG. 3.

5. The crystalline molecular sieve of claim 1 where the X-ray diffraction pattern in Table III contains at least the d-spacings set forth in the following Table II

TABLE II

| 2θ | d, (A) | 100 × I/Io |
|---|---|---|
| 7.9 | 11.17 | 59 |
| 8.8 | 10.03 | 37 |
| 11.9 | 7.46 | 9 |
| 12.5 | 7.10 | 4 |
| 13.2 | 6.71 | 4 |
| 13.9 | 6.38 | 9 |
| 14.7 | 6.02 | 9 |
| 15.5 | 5.72 | 6 |
| 15.9 | 5.58 | 8 |
| 17.2 | 5.14 | 3 |
| 17.7 | 5.01 | 5 |
| 19.2 | 4.62 | 5 |
| 20.0 | 4.45 | 2 |
| 20.3 | 4.37 | 9 |
| 20.8 | 4.27 | 9 |
| 22.2 | 4.01 | 5 |
| 23.1 | 3.85 | 100 |
| 23.7 | 3.76 | 34 |
| 23.9 | 3.73 | 44 |
| 24.4 | 3.66 | 26 |
| 25.8 | 3.448 | 9 |
| 26.9 | 3.314 | 8 |
| 27.4 | 3.258 | 3 |
| 29.2 | 3.057 | 9 |
| 29.9 | 2.989 | 12 |
| 30.3 | 2.951 | 5 |
| 32.7 | 2.738 | 3 |
| 34.4 | 2.609 | 3 |
| 34.8 | 2.576 | 2 |
| 35.7 | 2.517 | 3 |
| 36.0 | 2.495 | 6 |
| 37.2 | 2.418 | 2 |
| 37.4 | 2.407 | 3 |
| 37.5 | 2.400 | 3 |
| 45.0 | 2.015 | 7 |
| 45.2 | 2.005 | 9 |
| 46.4 | 1.956 | 2 |
| 47.4 | 1.919 | 3 |
| 48.5 | 1.876 | 4 |
| 48.7 | 1.871 | 2 |
| 51.8 | 1.766 | 2 |
| 54.6 | 1.680 | 2 |
| 55.0 | 1.671 | 3 |
| 55.2 | 1.664 | 3. |

6. The crystalline molecular sieve of claim 1 where the X-ray diffraction pattern in Table III contains at least the d-spacings set forth in the following Table IV

TABLE IV

| 2θ | d, (A) | 100 × I/Io |
|---|---|---|
| 8.0 | 11.10 | 100 |
| 8.9 | 9.97 | 59 |
| 11.9 | 7.46 | 4 |
| 13.3 | 6.68 | 4 |
| 14.0 | 6.34 | 11 |
| 14.9 | 5.97 | 13 |
| 15.6 | 5.69 | 8 |
| 16.0 | 5.56 | 10 |
| 17.8 | 4.97 | 6 |
| 19.3 | 4.60 | 4 |
| 20.4 | 4.36 | 5 |
| 20.9 | 4.25 | 8 |
| 22.3 | 3.99 | 4 |
| 23.2 | 3.84 | 62 |
| 23.3 | 3.82 | 59 |

TABLE IV-continued

| 2Θ | d, (A) | 100 × I/Io |
|---|---|---|
| 23.8 | 3.75 | 24 |
| 24.0 | 3.71 | 32 |
| 24.4 | 3.66 | 21 |
| 25.7 | 3.474 | 3 |
| 25.9 | 3.438 | 4 |
| 26.7 | 3.334 | 4 |
| 29.3 | 3.048 | 7 |
| 29.9 | 2.989 | 9 |
| 30.4 | 2.943 | 5 |
| 32.8 | 2.731 | 3 |
| 36.1 | 2.487 | 4 |
| 37.5 | 2.400 | 3 |
| 45.1 | 2.010 | 5 |
| 45.6 | 1.991 | 8 |
| 48.6 | 1.873 | 4 |
| 48.8 | 1.868 | 3 |
| 53.5 | 1.713 | 5. |

7. The crystalline molecular sieve of claim 1 where the X-ray diffraction pattern in Table III contains at least the d-spacings set forth in the following Table V

TABLE V

| 2Θ | d, (A) | 100 × I/Io |
|---|---|---|
| 7.9–8.0 | 11.17–11.10 | 36–100 |
| 8.8–8.9 | 10.03–9.97 | 25–60 |
| 9.0–9.1 | 9.83–9.72 | 14–18 |
| 11.8–12.0 | 7.50–7.38 | 2–11 |
| 12.5–12.6 | 7.10–7.03 | 3–6 |
| 13.2–13.3 | 6.71–6.68 | 4–7 |
| 13.9–14.0 | 6.38–6.34 | 6–12 |
| 14.7–14.9 | 6.02–5.97 | 7–16 |
| 15.5–15.6 | 5.72–5.69 | 6–12 |
| 15.9–16.0 | 5.58–5.56 | 6–14 |
| 16.5–16.6 | 5.37–5.34 | 2–3 |
| 17.2–17.3 | 5.14–5.13 | 2–5 |
| 17.7–17.8 | 5.01–4.97 | 4–6 |
| 19.2–19.3 | 4.62–4.60 | 4–8 |
| 19.9–20.0 | 4.46–4.45 | 2–3 |
| 20.3–20.5 | 4.37–4.33 | 5–9 |
| 20.8–21.0 | 4.27–4.23 | 8–13 |
| 21.7–21.8 | 4.10–4.08 | 1–3 |
| 22.1–22.3 | 4.02–3.99 | 3–7 |
| 23.1–23.3 | 3.85–3.82 | 62–100 |
| 23.7–23.8 | 3.76–3.75 | 24–34 |
| 23.9–24.0 | 3.73–3.71 | 32–50 |
| 24.4–24.5 | 3.66–3.63 | 21–31 |
| 25.4–25.7 | 3.507–3.474 | 3–5 |
| 25.7–26.0 | 3.474–3.427 | 3–9 |
| 26.3–26.7 | 3.389–3.334 | sh–8 |
| 26.7–27.1 | 3.339–3.290 | 4–16 |
| 27.3–27.7 | 3.267–3.220 | 3–8 |
| 28.0–28.4 | 3.187–3.143 | 2–3 |
| 29.9–29.4 | 3.057–3.039 | 7–10 |
| 29.9–30.1 | 2.989–2.969 | 9–16 |
| 30.3–30.4 | 2.951–2.943 | 5–6 |
| 32.7–32.8 | 2.738–2.731 | 3–4 |
| 34.3–34.6 | 2.614–2.592 | 3–7 |
| 34.6–35.0 | 2.592–2.564 | 2–3 |
| 35.6–35.8 | 2.522–2.508 | 2–4 |
| 36.0–26.3 | 2.495–2.475 | 3–9 |
| 37.1–27.3 | 2.423–2.411 | 2–3 |
| 37.4–37.7 | 2.407–2.386 | 3–5 |
| 41.3–41.5 | 2.186–2.176 | 2–3 |
| 45.0–45.2 | 2.015–2.005 | 5–9 |
| 45.3–45.6 | 2.002–1.991 | 6–11 |
| 46.4–46.5 | 1.956–1.953 | 2–3 |
| 47.3–47.6 | 1.922–1.910 | 2–3 |
| 48.4–48.6 | 1.881–1.873 | 3–4 |
| 48.7–48.8 | 1.871–1.868 | 2–3 |
| 51.8–52.0 | 1.766–1.759 | 1–3 |
| 53.5 | 1.713 | 5 |
| 54.4–54.7 | 1.687–1.678 | 2–3 |
| 54.9–55.1 | 1.672–1.667 | 3–5 |
| 55.2–55.5 | 1.664–1.656 | 3–4. |

8. The crystalline molecular sieve of claim 1 where the molecular sieve has been calcined to remove at least some of any organic templating agent present in the intracrystalline pore system.

9. A process for preparing a crystalline molecular sieve having a three-dimensional microporous framework structure of $TiO_2$, $AlO_2$ and $SiO_2$ tetrahedral units, having an intracrystalline pore system where the pores have nominal diameters of about 6 Angstroms and having a chemical composition on an anhydrous basis expressed by the formula:

$$mR: (Ti_xAl_ySi_z)O_2$$

where "R" represents at least one organic templating agent present in the intracrystalline pore system; "m" represents the moles of "R" present per mole of $(Ti_xAl_ySi_z)O_2$ and has a value from zero to about 0.3; and "x", "y", and "z" represent the mole fractions of titanium, aluminum, and silicon, respectively, present as tetrahedral oxides, said mole fractions being such that they are within the compositional area defined by points A, B, C, and D of the ternary diagram of FIG. 1 and having a characteristic X-ray pattern as set forth in Table III

TABLE III

| 2Θ | d, (Å) | Relative Intensity |
|---|---|---|
| 7.9–8.0 | 11.17–11.10 | m-vs |
| 8.8–8.9 | 10.03–9.97 | m |
| 23.1–23.3 | 3.85–3.82 | m-vs |
| 23.7–23.8 | 3.76–3.75 | m |
| 23.9–24.0 | 3.73–3.71 | m |
| 24.4–24.5 | 3.66–3.63 | m | the process comprising providing a reaction mixture composition at an effective temperature and for an effective time sufficient to produce the molecular sieve, the reaction mixture composition comprising reactive sources of aluminum, silicon and titanium, the titanium source selected from the group consisting of titanium alkoxides, water soluble titanates and titanium chelates, the reaction mixture composition expressed in terms of molar oxide ratios by the formula:

$$aR: (Ti_uAl_vSi_w)O_2:bH_2O$$

where "R" is an organic templating agent; "a" is an effective amount of "R"; "b" has a value from greater than zero to about 5000; and "u", "v" and "w" represent the mole fractions of titanium, aluminum, and silicon, respectively, in the $(Ti_uAl_vSi_w)O_2$ constituent, and are within the tetragonal compositional area defined by points E, F, G and H of FIG. 4.

10. The process of claim 9 where the source of silicon in the reaction mixture is silica.

11. The process of claim 9 where the source of aluminum in the reaction mixture is at least one compound selected from the group consisting of pseudo-boehmite and aluminum alkoxide.

12. The process of claim 11 where the aluminum alkoxide is aluminum isopropoxide.

13. The process of claim 9 where the organic templating agent is selected from the group consisting of quaternary ammonium or quaternary phosphonium compounds of the formula:

$$R_4X^+$$

where X is nitrogen or phosphorous and each R is an aryl group or an alkyl group, the alkyl group containing between 1 and about 8 carbon atoms.

14. The process of claim 9 where the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-diethylethanolamine; dicyclohexylamine; N,N-dimethylethanolamine; choline; N,N-dimethylpiperazine; pyrrolidine; 1,4-diazabicyclo(2,2,2) octane; N-methylpiperidine; 3-methylpiperidine; N-methylcyclohexylamine; 3-methylpyridine; 4-methylpyridine; quinuclidine; N,N-dimethyl-1,4-diazabicyclo-(2,2,2) octane ion; tetramethylammonium ion; tetrabutylammonium ion, tetrapentylammonium ion; di-n-butylamine; neopentylamine; di-n-pentylamine; isopropylamine; t-butylamine; ethylenediamine and 2-imidazolidone; di-n-propylamine; and a polymeric quaternary ammonium salt $[(C_{14}H_{32}N_2)(OH)_2]_x$ wherein x is a value of at least 2.

* * * * *